US012703686B2

(12) United States Patent
Jung et al.

(10) Patent No.: US 12,703,686 B2
(45) Date of Patent: Aug. 11, 2026

(54) 4-METHOXY-2-PHENETHYL ISOINDOLINE-1-ONE DERIVATIVE AND COMPOSITION FOR TREATING NEUROLOGICAL DISEASES, COMPRISING SAME

(71) Applicants: CNG BIO CO., LTD., Cheongju-si (KR); CHUNGBUK NATIONAL UNIVERSITY INDUSTRY-ACADEMIC COOPERATION FOUNDATION, Cheongju-si (KR); GACHON UNIVERSITY OF INDUSTRY-ACADEMIC COOPERATION FOUNDATION, Seongnam-si (KR)

(72) Inventors: Jaekyung Jung, Cheongju-si (KR); Mi Kyeong Lee, Cheongju-si (KR); Dae Hee Lee, Cheongju-si (KR); Jae Kang Lee, Cheongju-si (KR); Sun Yeou Kim, Seoul (KR); Da Hye Yoon, Bucheon-si (KR); Seong Min Hong, Chungju-si (KR)

(73) Assignees: CNG BIO CO., LTD., Cheongju-si (KR); CHUNGBUK NATIONAL UNIVERSITY INDUSTRY-ACADEMIC COOPERATION FOUNDATION, Cheongju-si (KR);
(Continued)

( * ) Notice: Subject to any disclaimer, the term of this patent is extended or adjusted under 35 U.S.C. 154(b) by 501 days.

(21) Appl. No.: 18/028,110

(22) PCT Filed: Sep. 17, 2021

(86) PCT No.: PCT/KR2021/012793
§ 371 (c)(1),
(2) Date: Mar. 23, 2023

(87) PCT Pub. No.: WO2022/065823
PCT Pub. Date: Mar. 31, 2022

(65) Prior Publication Data

US 2023/0365501 A1 Nov. 16, 2023

(30) Foreign Application Priority Data

Sep. 23, 2020 (KR) ........................ 10-2020-0123284

(51) Int. Cl.
*C07D 209/44* (2006.01)
*A61P 25/28* (2006.01)

(52) U.S. Cl.
CPC ............ *C07D 209/44* (2013.01); *A61P 25/28* (2018.01)

(58) Field of Classification Search
CPC ............................... C07D 209/44; A61P 25/28
(Continued)

(56) References Cited

U.S. PATENT DOCUMENTS

2009/0275578 A1 11/2009 Clayton et al.

FOREIGN PATENT DOCUMENTS

JP 2012077030 A * 7/2012 ......... A61K 31/4035
KR 10-0935615 B1 1/2010
(Continued)

OTHER PUBLICATIONS

Milligan SR, Kalita JC, Pocock V, Van De Kauter V, Stevens JF, Deinzer ML, Rong H, De Keukeleire D. The endocrine activities of 8-prenylnaringenin and related hop (*Humulus lupulus* L.) flavonoids. The journal of clinical endocrinology & metabolism. Dec. 1, 2000;85(12):4912-5. (Year: 2000).*
(Continued)

*Primary Examiner* — Jeffrey S Lundgren
*Assistant Examiner* — Heather Dahlin
(74) *Attorney, Agent, or Firm* — Sughrue Mion, PLLC

(57) ABSTRACT

The present invention relates to: a novel 4-methoxy-2-phenethyl isoindolin-1-one derivative compound having the ability to promote the increase of nerve growth factor, the
(Continued)

ability to promote the growth of nerve cells, and antineuritic activity; and a composition for preventing, improving and treating neurological diseases, comprising the same.

9 Claims, 24 Drawing Sheets

(73) Assignees: GACHON UNIVERSITY OF INDUSTRY-ACADEMIC COOPERATION FOUNDATION, Seongnam-si (KR)

(58) Field of Classification Search
USPC .......................................................... 514/416
See application file for complete search history.

(56) References Cited

FOREIGN PATENT DOCUMENTS

KR 10-2014-0082052 A 7/2014
KR 10-2061526 B1 1/2020
KR 2061526 B1 * 1/2020 ............. A23K 10/30
WO 2006/020879 A1 2/2006

OTHER PUBLICATIONS

Erik Andrade-Jorge et al., “Isoindolines/isoindoline-1,3-diones as AChE inhibitors against Alzheimer’s disease, evaluated by an improved ultra-micro assay”, Medicinal Chemistry Research, Published online Jul. 30, 2018, pp. 2187-2198, vol. 27.
Junying Yuan et al., “Apoptosis in the nervous system”, Nature, Oct. 12, 2000, pp. 802-809, vol. 407.
International Search Report for PCT/KR2021/012793, dated Jan. 7, 2022.
Extended European search report (EESR) issued on Sep. 6, 2024 for related European Patent Application No. 21872851.7.

* cited by examiner

4-METHOXY-2-PHENETHYL ISOINDOLINE-1-ONE DERIVATIVE AND COMPOSITION FOR TREATING NEUROLOGICAL DISEASES, COMPRISING SAME

CROSS REFERENCE TO RELATED APPLICATIONS

This application is a National Stage of International Application No. PCT/KR2021/012793 filed Sep. 17, 2021, claiming priority based on Korean Patent Application No. 10-2020-0123284 filed Sep. 23, 2020, the entire disclosures of which are incorporated herein by reference.

TECHNICAL FIELD

The present invention relates to: a novel 4-methoxy-2-phenethyl isoindolin-1-one derivative compound having the ability to promote the increase of nerve growth factor, the ability to promote the growth of nerve cells, and antineuritic activity; and a composition for preventing, improving and treating neurological diseases, comprising the same.

BACKGROUND ART

Recently, with the rapid increase of the elderly population, the number of patients with various neurodegenerative brain diseases is increasing, and interest in treatment and prevention thereof is increasing. Neurodegenerative disease is a disease that causes several pathologies such as motor disorders, memory disorders, and cognitive disorders due to reduced or lost functions of nerve cells. A large number of nerve cells die every day not only in patients with neurological diseases but also in the brains of normal adults, and the number of nerve cells that die increases exponentially with aging.

Major diseases belonging to neurodegenerative diseases include Alzheimer's disease, Parkinson's disease, Lou Gehrig's disease, Huntington's disease, and the like, and the pathogenesis of these diseases has not been completely elucidated to date. Acetylcholinesterase inhibitors or NMDA (N-methyl-D-aspartate) receptor antagonists, etc., are used as a therapeutic agent for Alzheimer's disease, and L-dopa, dopamine agonists, MAO-B inhibitors, or COMT inhibitors, etc., are used as a therapeutic agent for Parkinson's disease, and dopamine D2 receptors and the like are used as a therapeutic agent for Huntington's disease. However, since all of the therapeutic agents target the neurotransmission process, the method using the therapeutic agents merely relieves symptoms rather than fundamental treatment. Therefore, new drugs capable of fundamental treatment have been continuously required.

On the other hand, it is known that neurological diseases are closely related to the deterioration of the function of brain nerve cells and the death of nerve cells (Korean Patent No. 10-0935615). The present inventors have found that the ability to promote the increase of nerve growth factor, the ability to promote the growth of nerve cells, and antineuritic activity of a 4-methoxy-2-phenethyl isoindolin-1-one derivative were excellent, thereby completing the present invention.

PRIOR ART DOCUMENT

Patent Document (Patent Document 1) Korean Patent No. 10-0935615

Non-Patent Document (Non-Patent Document 1) Yuan and Yankner, Nature. 407, 802-809, 2000

DETAILED DESCRIPTION OF INVENTION

Technical Problem

An object of the present invention is to provide a novel compound and a pharmaceutically acceptable salt thereof having the ability to promote the increase of nerve growth factor, the ability to promote the growth of nerve cells, and antineuritic activity.

In addition, another object of the present invention is to provide a composition for preventing, improving or treating neurological diseases, comprising the compound and pharmaceutically acceptable salt thereof.

Solution to Problem

The present invention provides a compound represented by Formula 9 below or a pharmaceutically acceptable salt thereof.

[Formula 9]

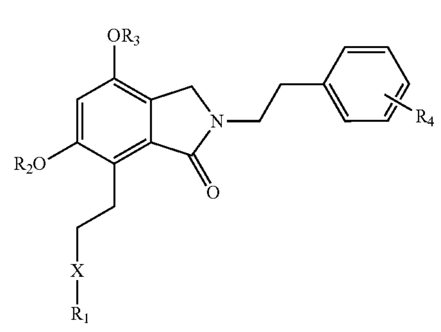

in the formula, $R_1$ is hydrogen, alkyl, alkenyl, alkynyl, hydroxy, alkoxy, hydroxyalkyl, alkoxyalkyl, or —N(Ra)(Rb); $R_2$, $R_3$, $R_4$, Ra and Rb are each independently hydrogen or alkyl; and X is a single bond or a double bond.

In addition, the present invention provides a composition for preventing, improving or treating neurological diseases, comprising the compound represented by Formula 9 and pharmaceutically acceptable salt thereof.

Effects of Invention

The novel compound of the present invention has the ability to promote the increase of nerve growth factor, the ability to promote the growth of nerve cells, and antineuritic activity.

Therefore, a composition comprising the novel compound of the present invention can be used as a pharmaceutical composition, a food composition and a feed composition having effects of preventing, improving and treating neurological diseases.

BEST MODE FOR CARRYING OUT THE INVENTION

Figure 1A:
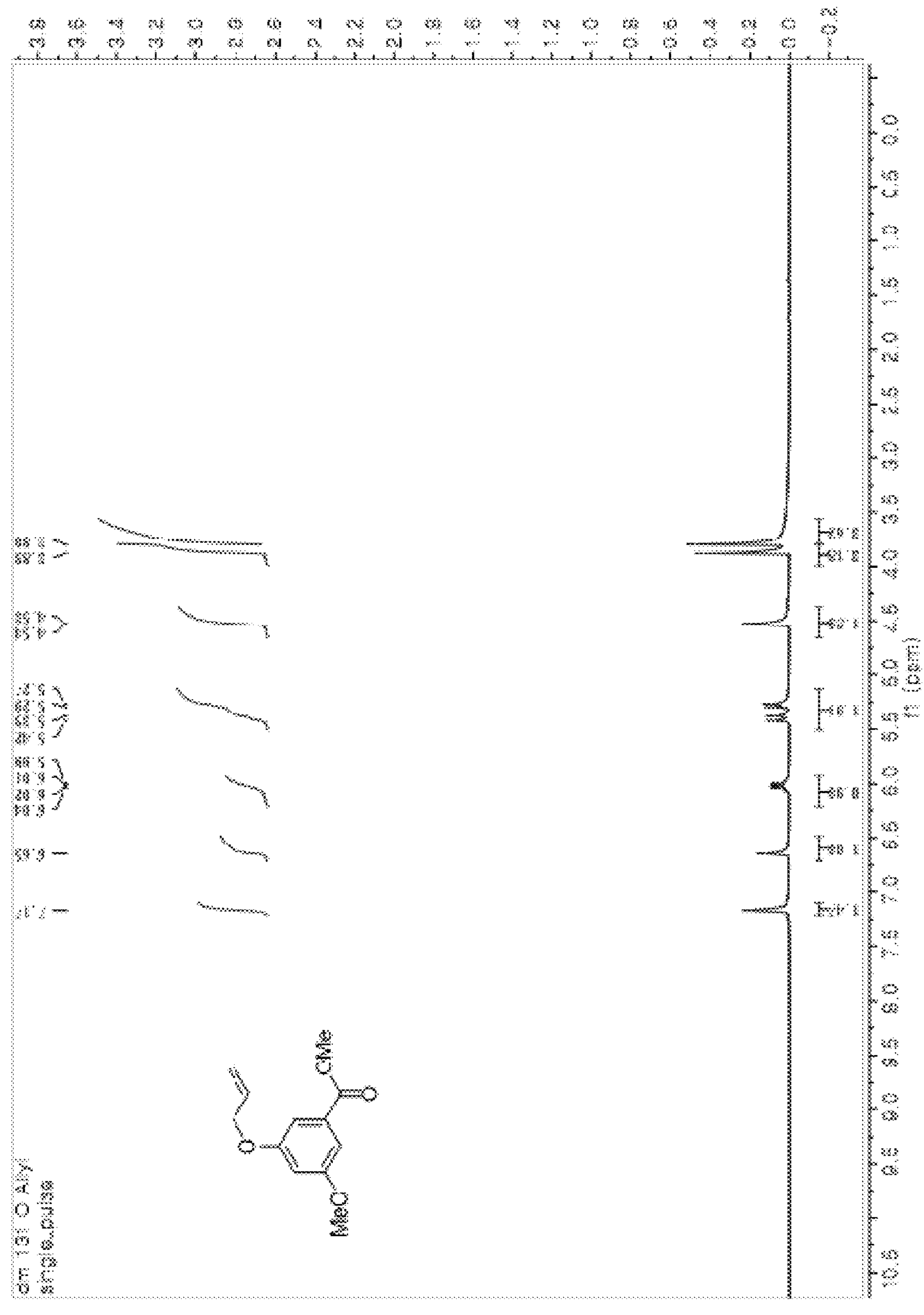
FIGS. 1*a* and 1*b* show the results of $^{1}H$ NMR and $^{13}C$ NMR analysis of the compound of Formula 1.
Figure 1B:
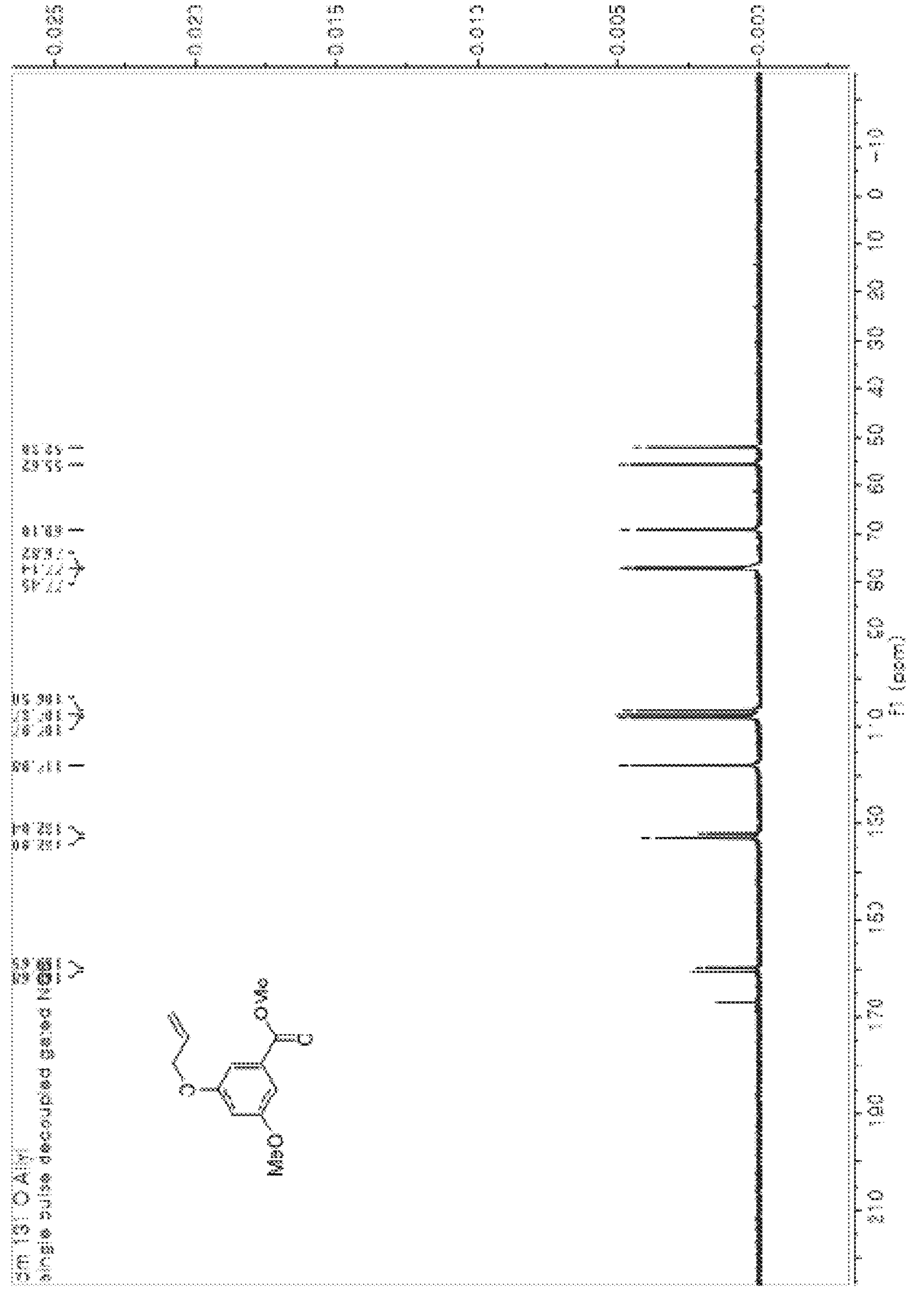
Figure 2A:
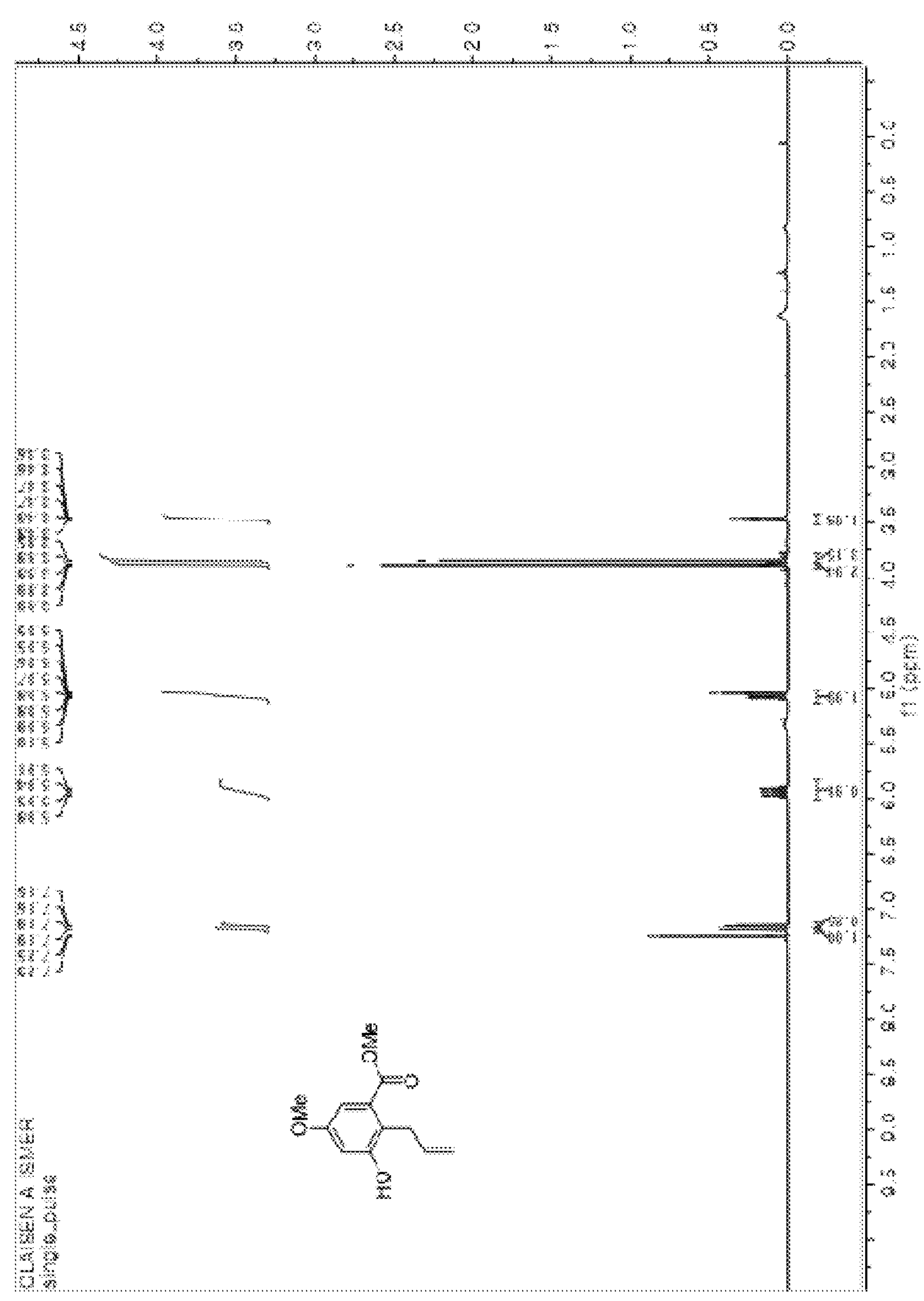
FIGS. 2*a* and 2*b* show the results of $^{1}H$ NMR and $^{13}C$ NMR analysis of the compound of Formula 2.
Figure 2B:
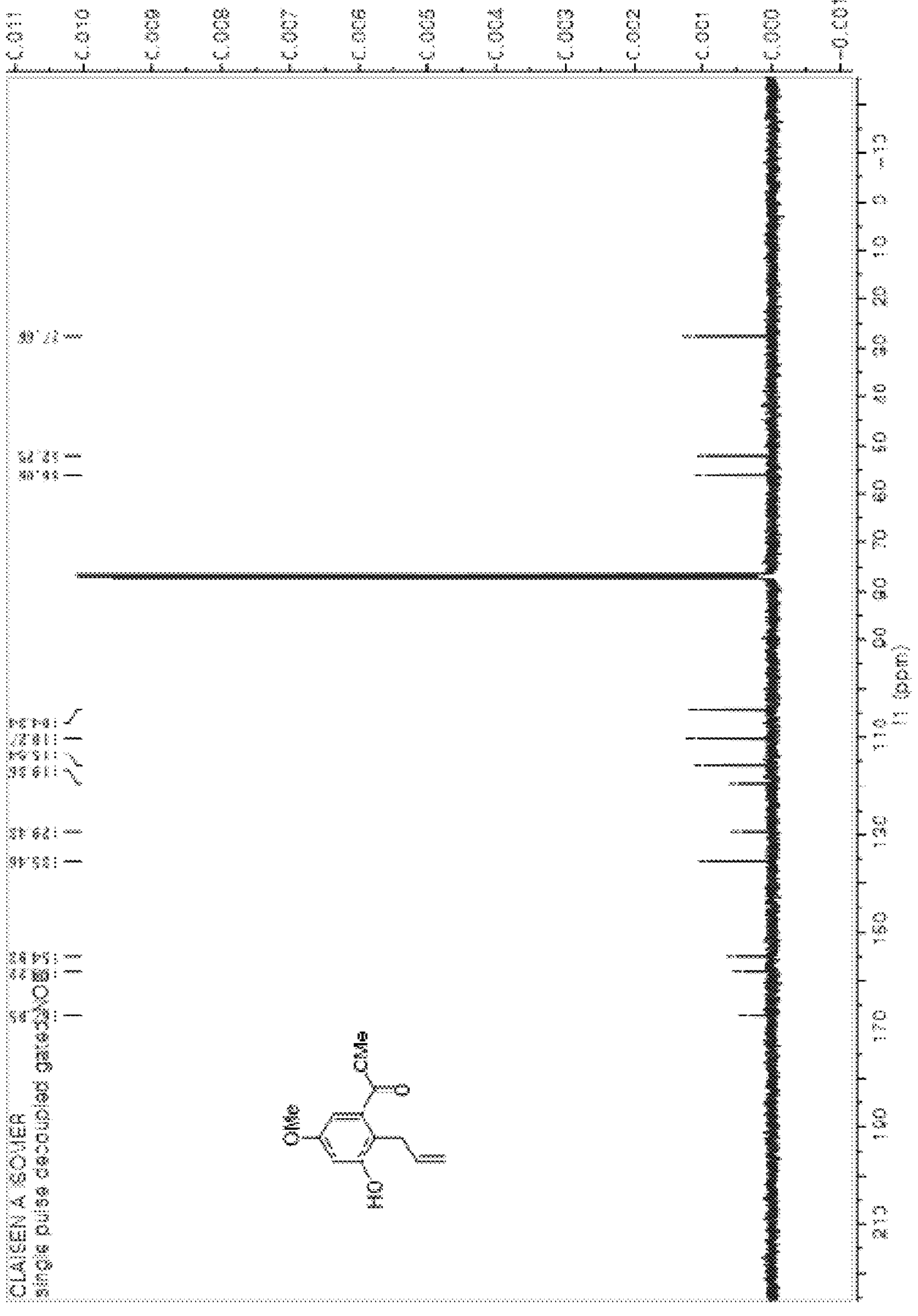
Figure 3A:
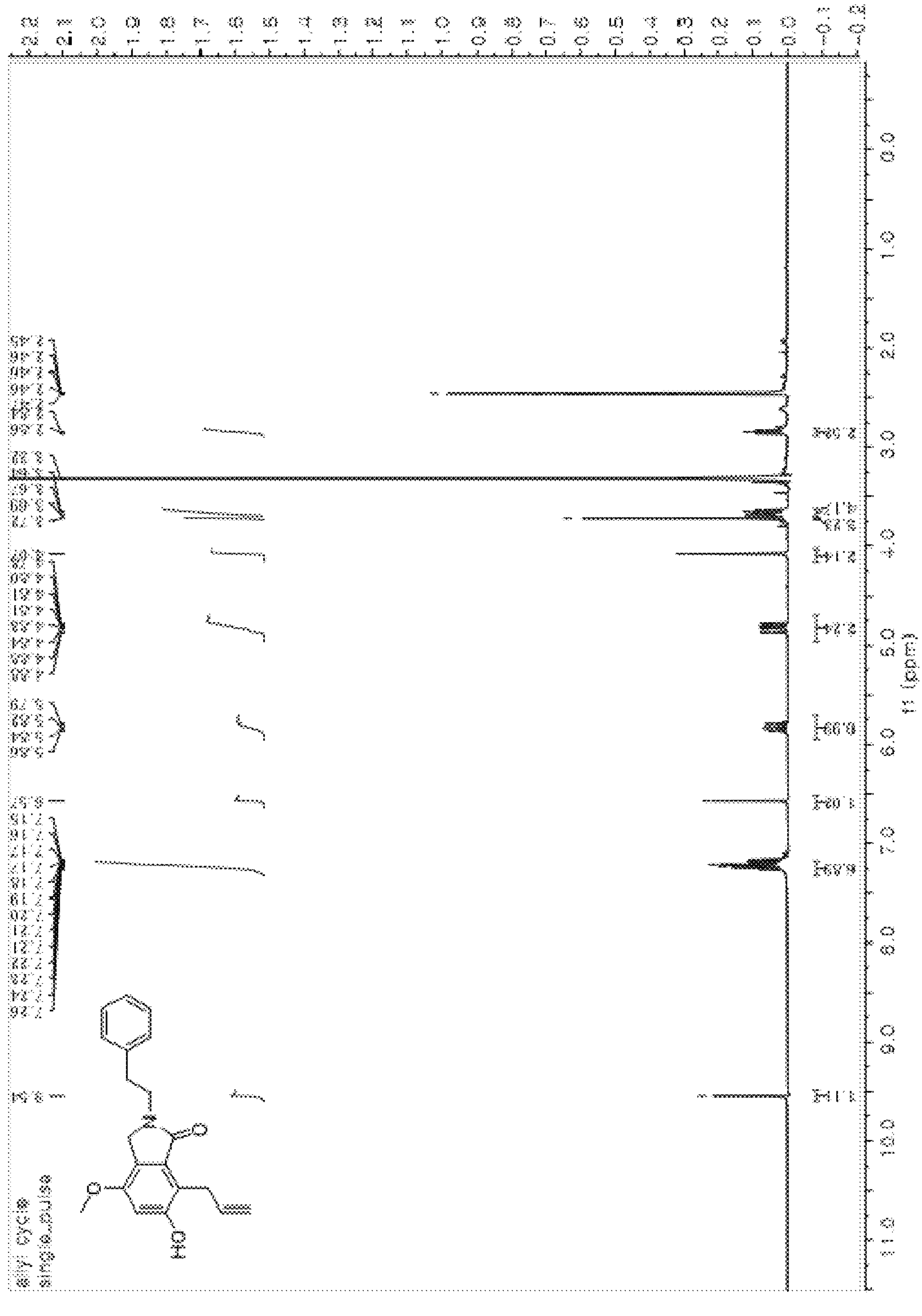
FIGS. 3*a* and 3*b* show the results of $^{1}H$ NMR and $^{13}C$ NMR analysis of the compound of Formula 3.
Figure 3B:
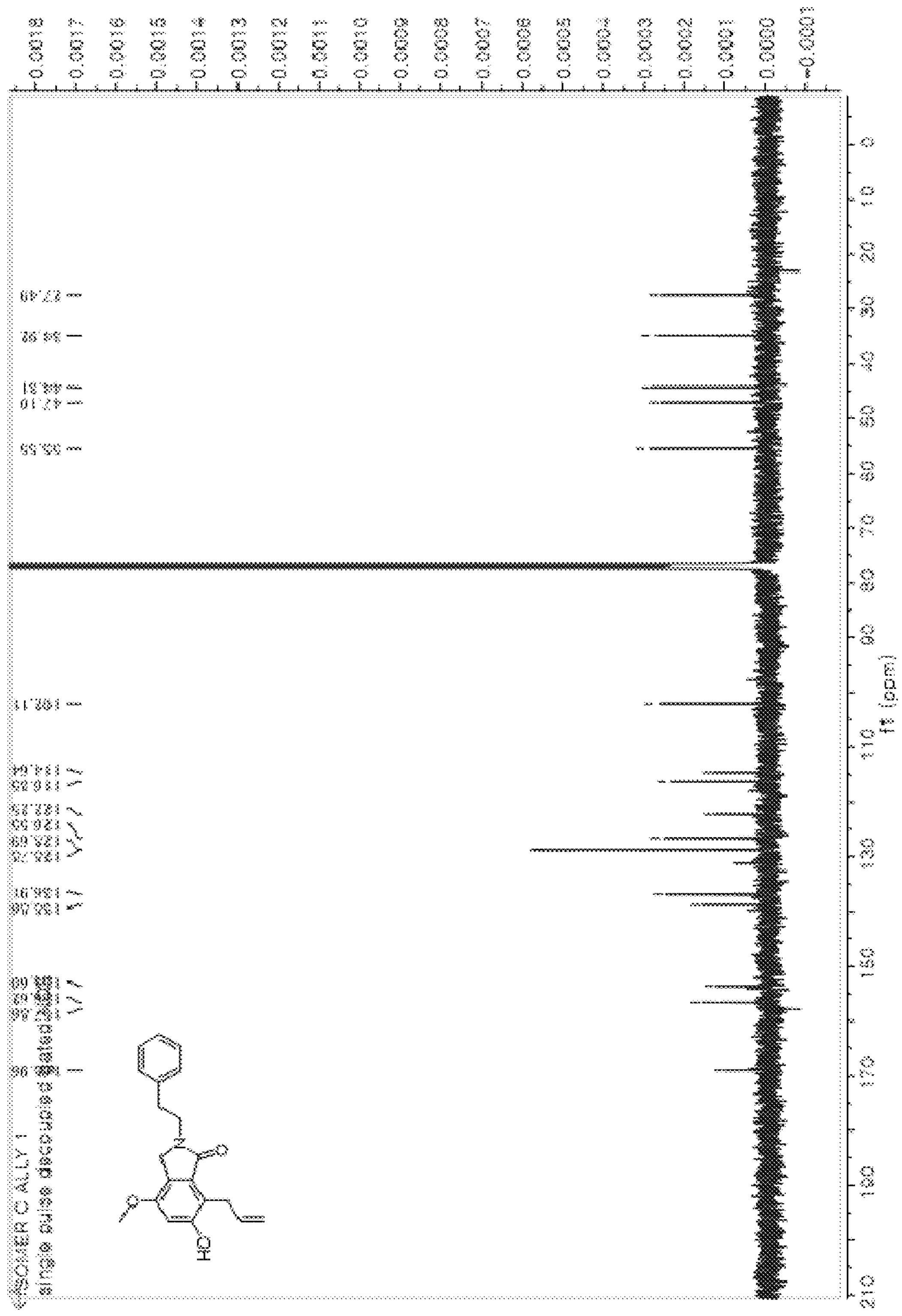
Figure 4A:
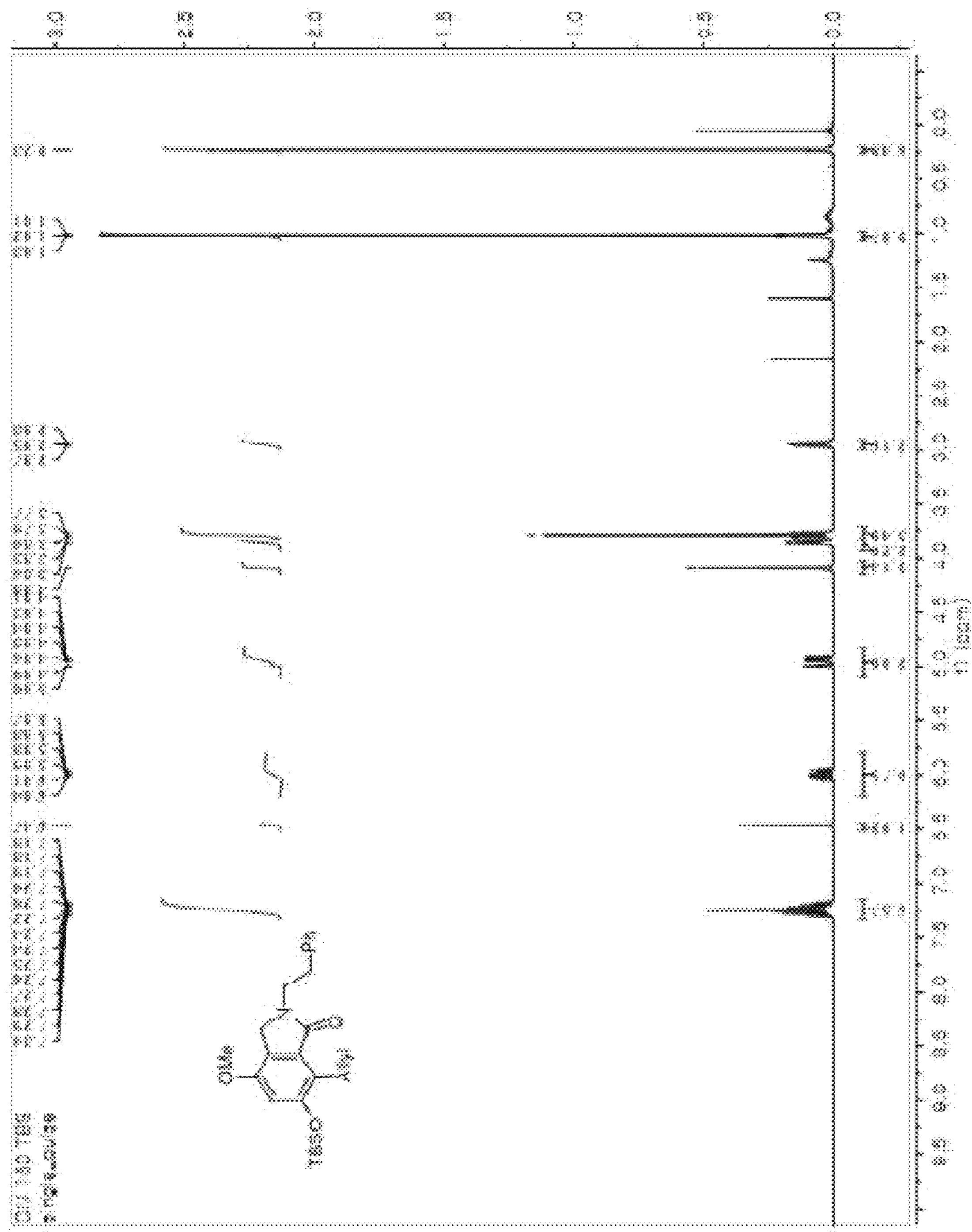
FIGS. 4*a* and 4*b* show the results of $^{1}H$ NMR and $^{13}C$ NMR analysis of the compound of Formula 4.
Figure 4B:
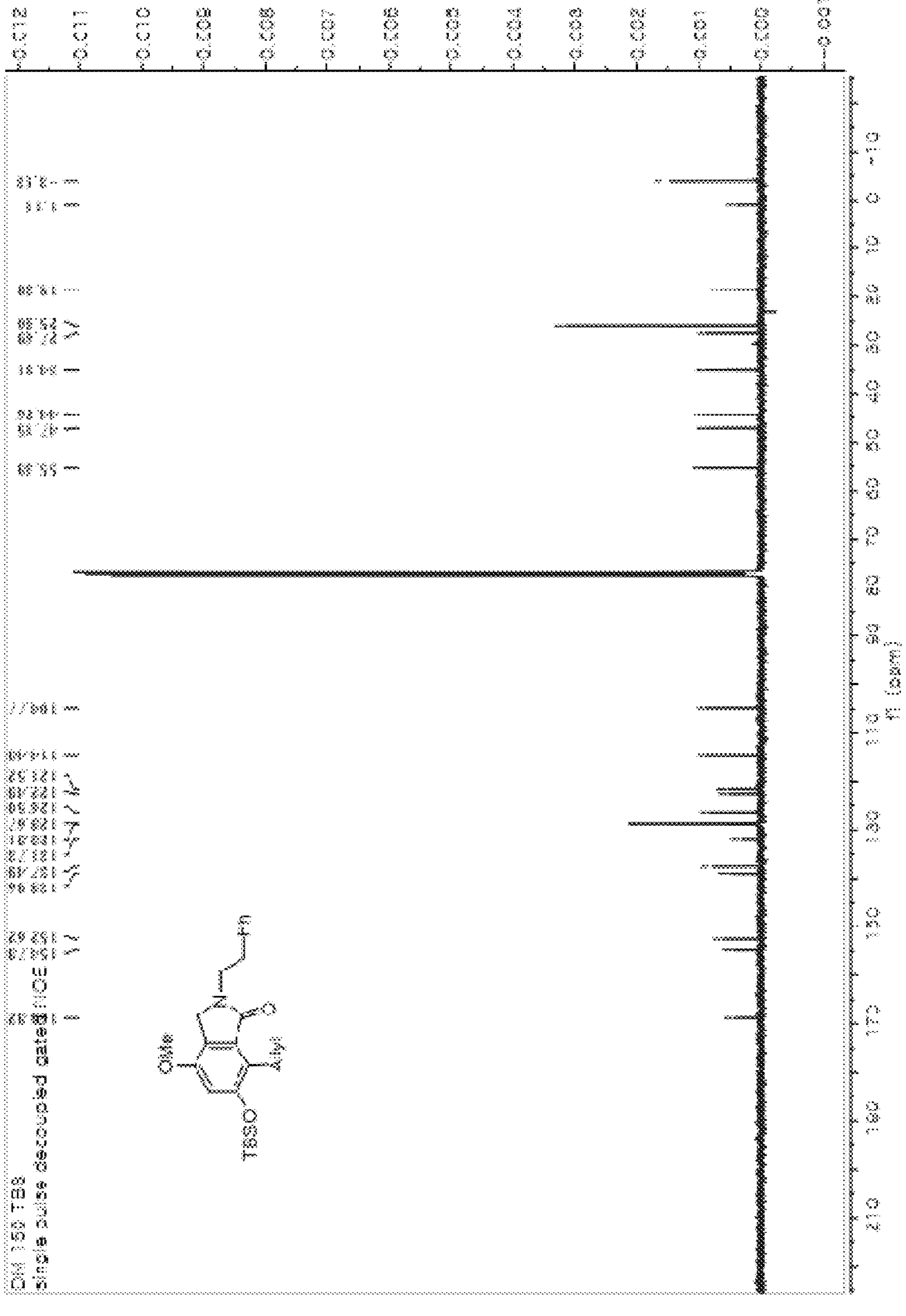
Figure 5A:
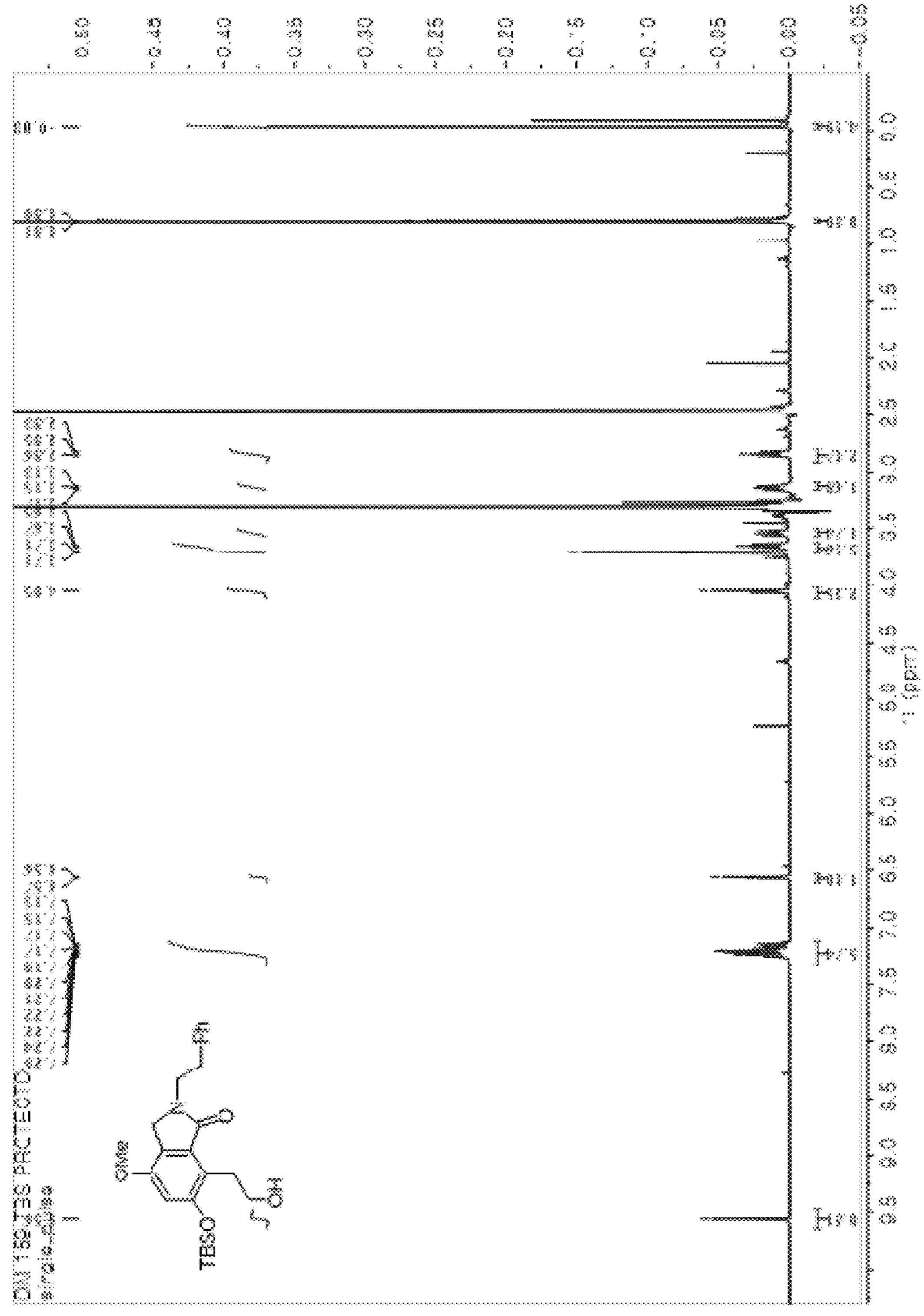
FIGS. 5*a* and 5*b* show the results of $^{1}H$ NMR and $^{13}C$ NMR analysis of the compound of Formula 5.
Figure 5B:
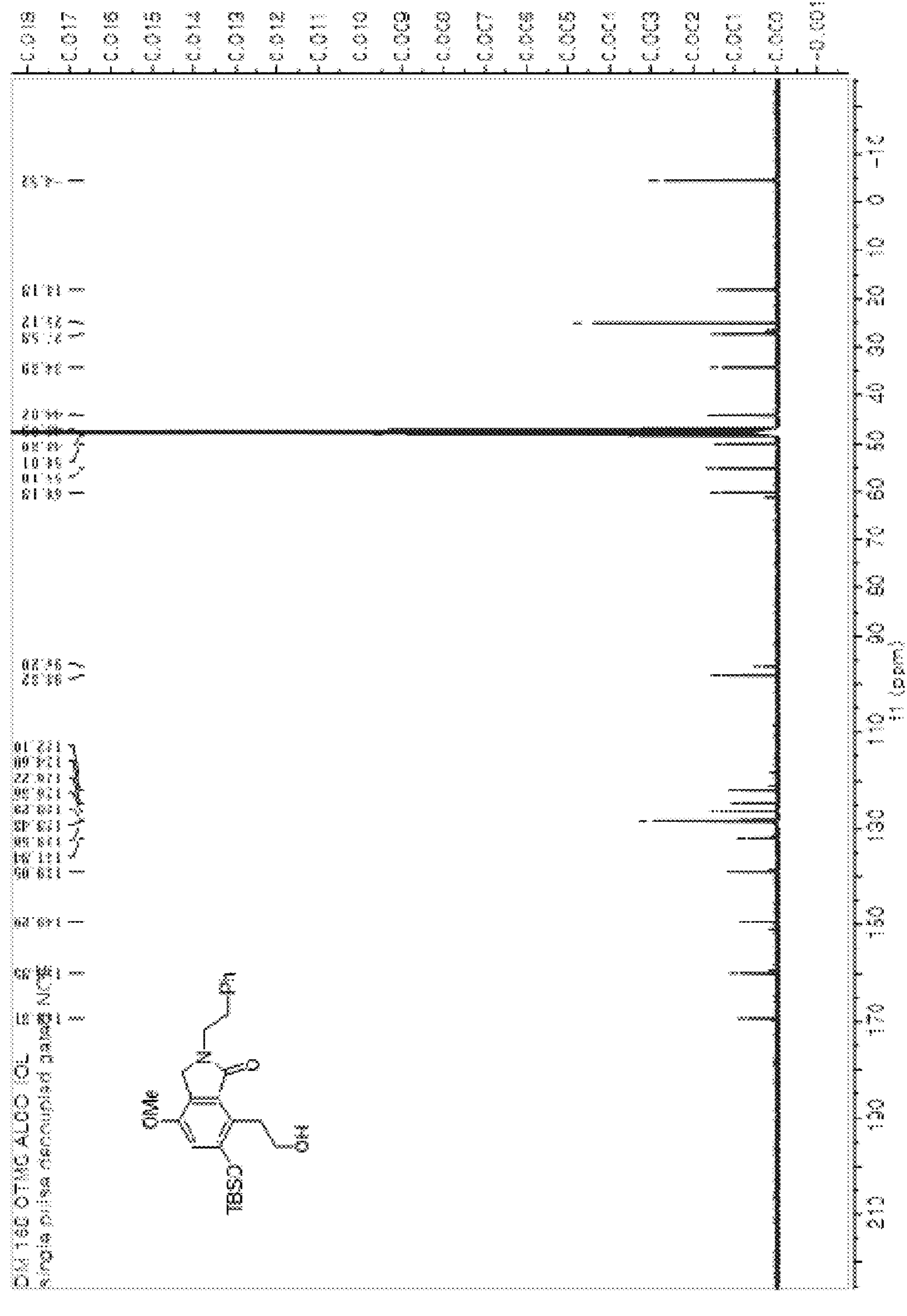
Figure 6A:
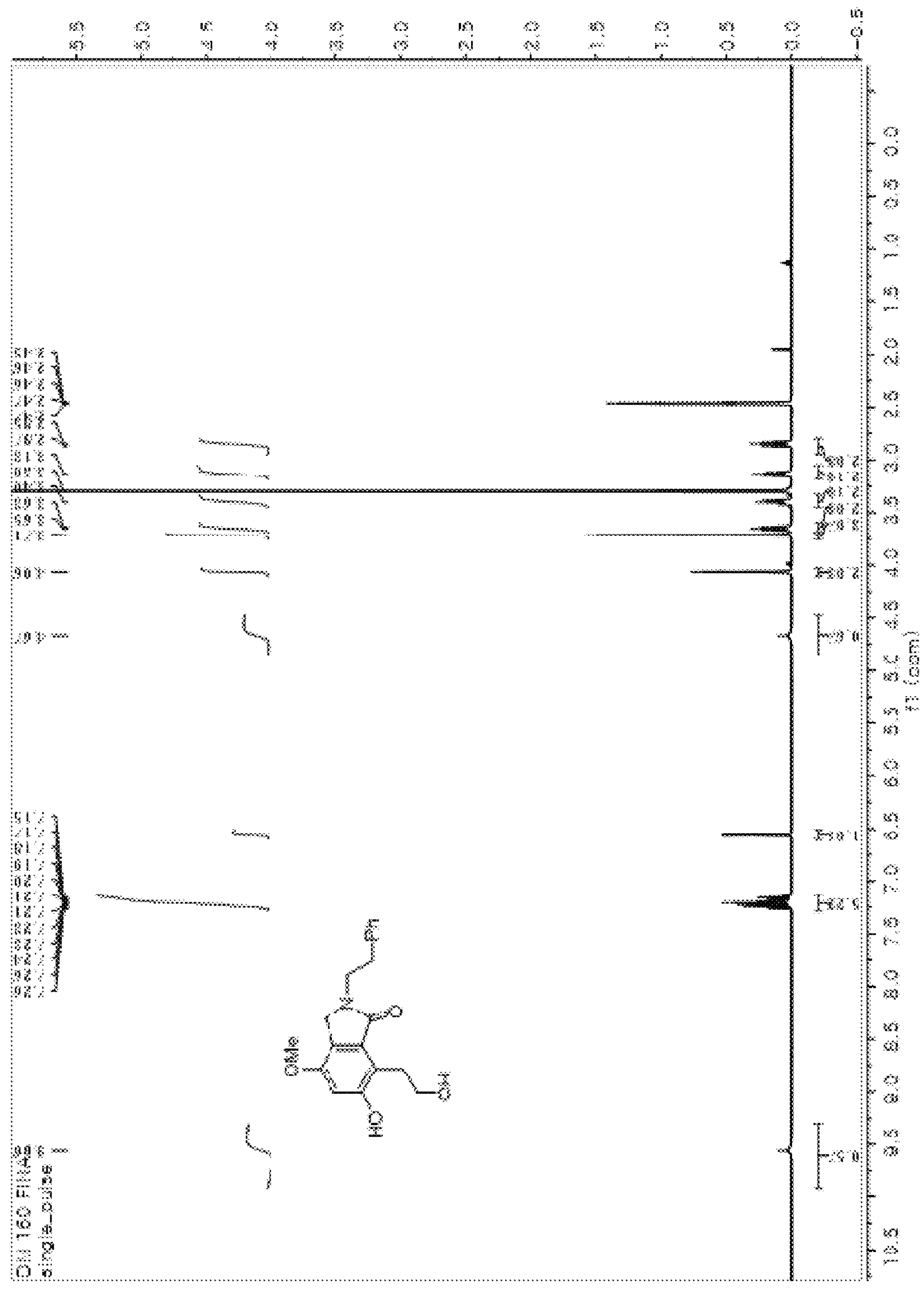
FIGS. 6*a* and 6*b* show the results of $^{1}H$ NMR and $^{13}C$ NMR analysis of the compound of Formula 6.
Figure 6B:
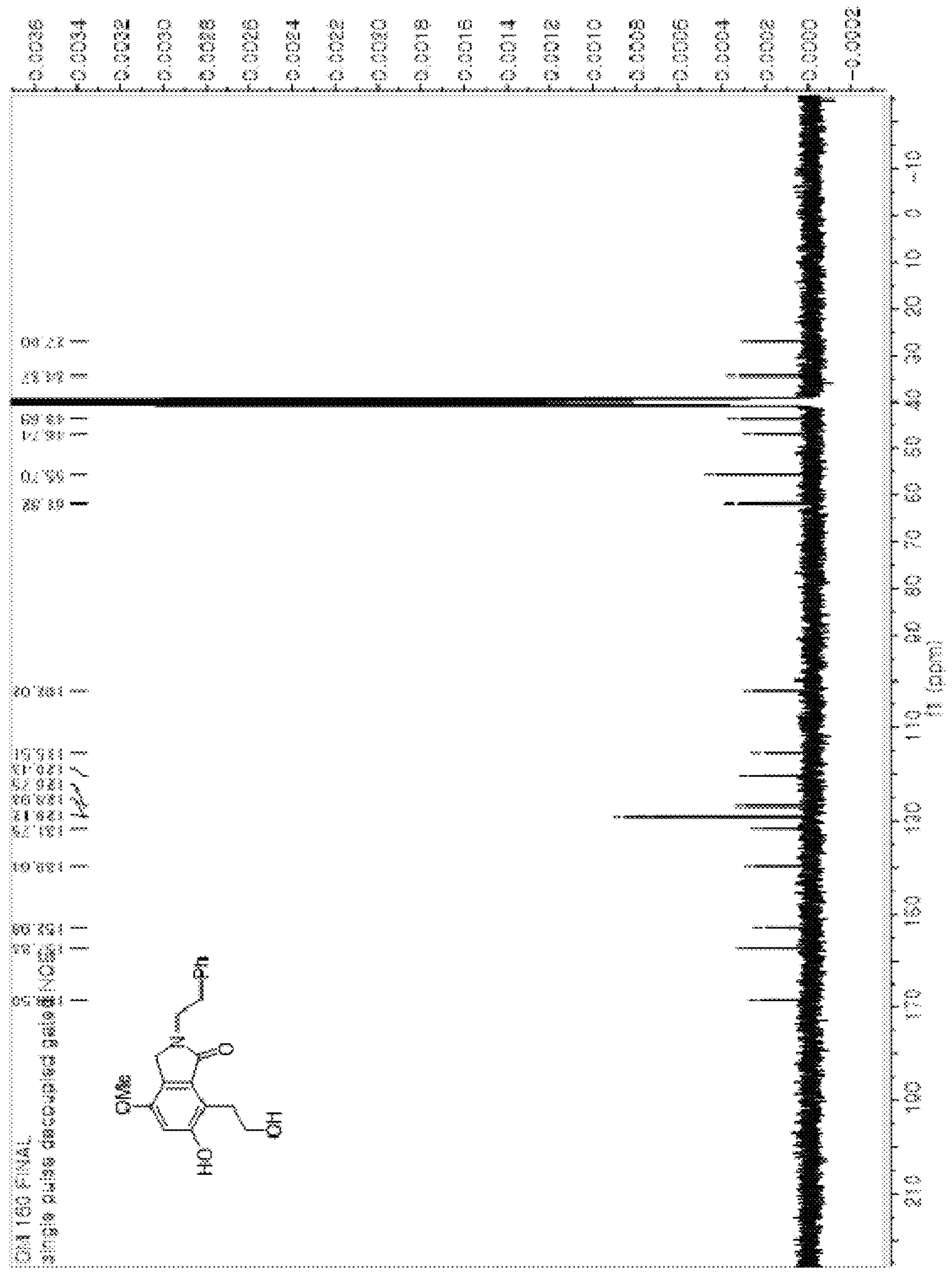
Figure 7A:
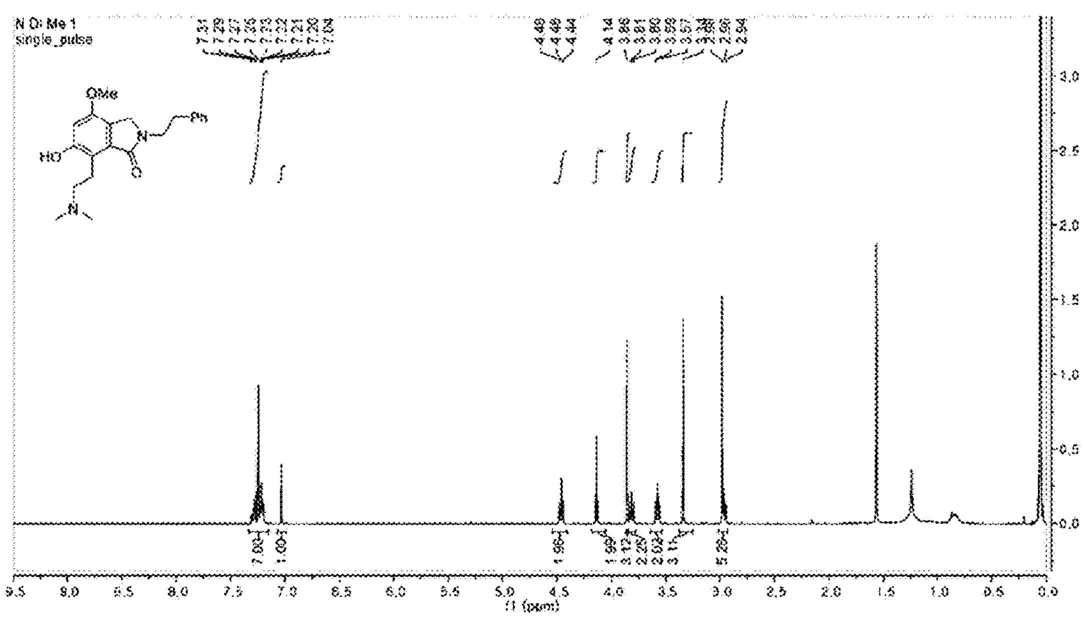
FIGS. 7*a* and 7*b* show the results of $^{1}H$ NMR and $^{13}C$ NMR analysis of the compound of Formula 7.
Figure 7B:
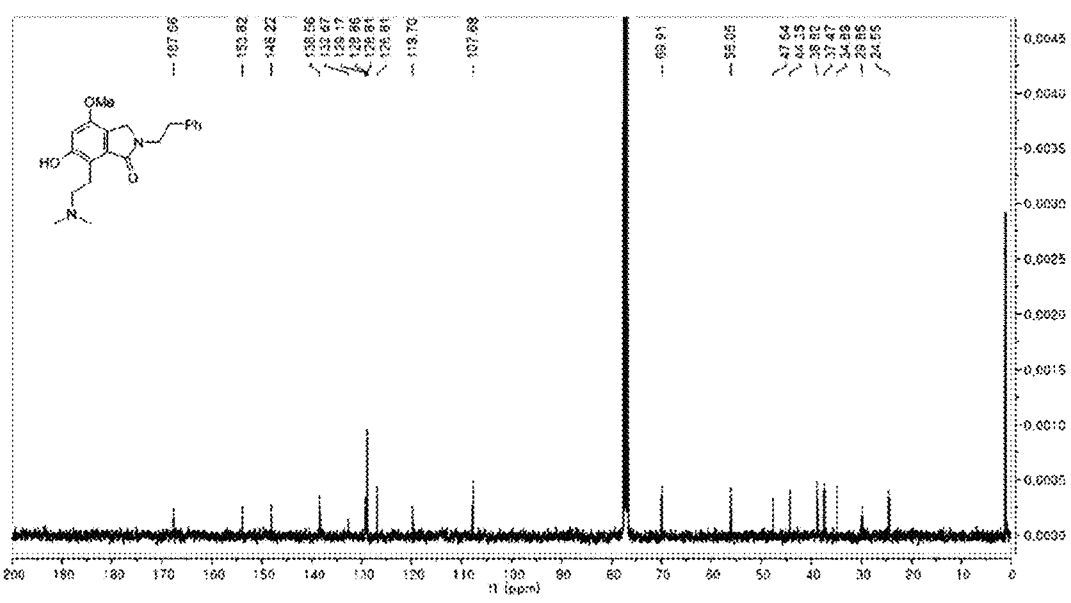
Figure 8A:
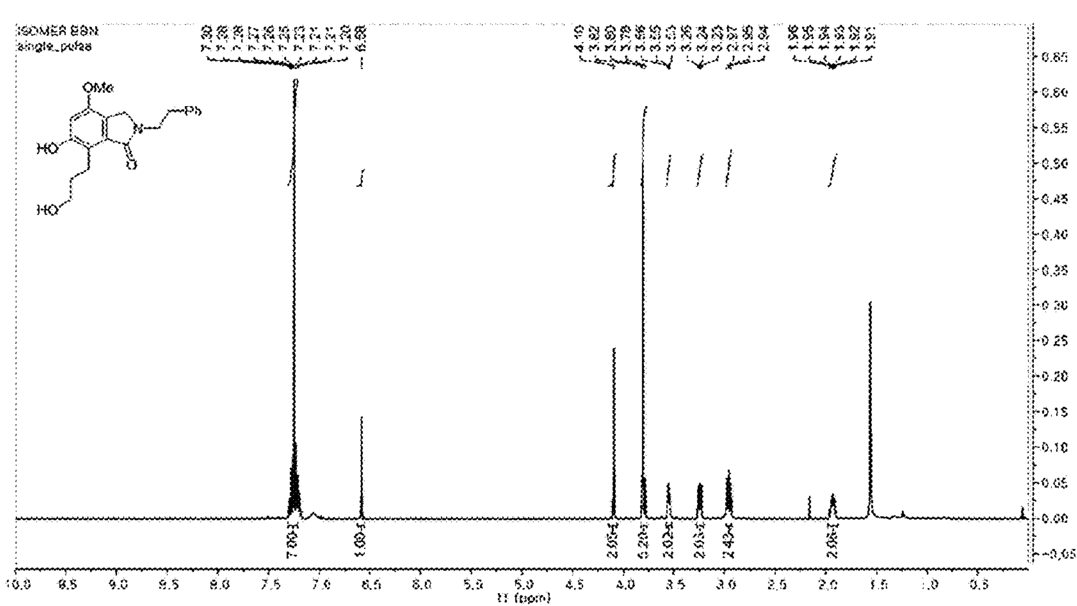
FIGS. 8*a* and 8*b* show the results of $^{1}H$ NMR and $^{13}C$ NMR analysis of the compound of Formula 8.
Figure 8B:
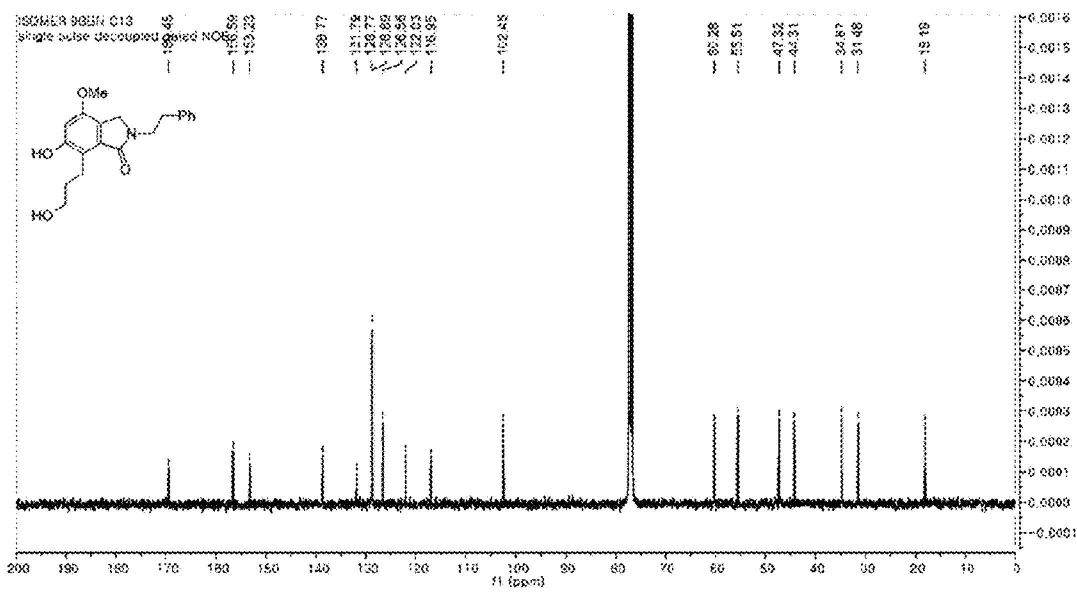

Hereinafter, with reference to the accompanying drawings, embodiments and examples of the present disclosure will be described in detail so that those of ordinary skill in the art to which the present invention belongs can easily practice the present invention. However, the present disclosure may be implemented in various forms and is not limited to the embodiments and examples described herein.

Throughout the present specification, when a certain part "includes" a certain component, it means that other components may be further included, rather than excluding other components, unless otherwise stated.

The present invention provides a compound represented by Formula 9 below or a pharmaceutically acceptable salt thereof.

[Formula 9]

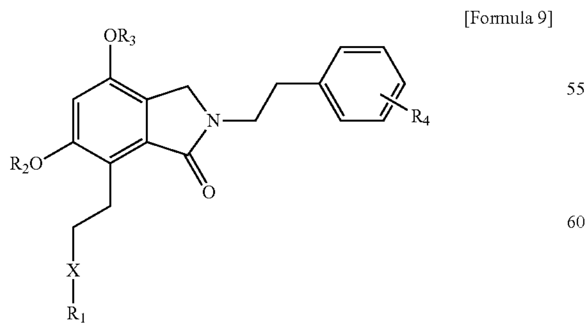

in the formula, $R_1$ is hydrogen, alkyl, alkenyl, alkynyl, hydroxy, alkoxy, hydroxyalkyl, alkoxyalkyl, or —N(Ra)(Rb); $R_2$, $R_3$, $R_4$, Ra and Rb are each independently hydrogen or alkyl; and X is a single bond or a double bond.

In one embodiment, $R_1$ may be hydrogen, alkyl, alkenyl, alkynyl, hydroxy, alkoxy, hydroxyalkyl, alkoxyalkyl, or —N(Ra)(Rb); Ra and Rb may be each independently hydrogen or alkyl; $R_2$ and $R_4$ may be hydrogen; $R_3$ may be alkyl; and X may be a single bond or a double bond.

In one embodiment, $R_1$ may be $C_1$-$C_6$ alkyl, hydroxy, $C_1$-$C_6$ hydroxyalkyl, or —N(Ra)(Rb); Ra and Rb may be each independently $C_1$-$C_6$ alkyl; $R_2$ and $R_4$ may be hydrogen; $R_3$ may be $C_1$-$C_6$ alkyl; and X may be a single bond or a double bond.

In one embodiment, $R_1$ may be hydroxy, —$CH_2OH$, or —$N(CH_3)(CH_3)$; $R_2$ and $R_4$ may be hydrogen; $R_3$ may be methyl; and X may be a single bond.

In one embodiment, $R_1$ may be methyl; $R_2$ and $R_4$ may be hydrogen; $R_3$ may be methyl; and X may be a double bond.

As used herein, the term "pharmaceutically acceptable salt" refers to a salt according to one aspect of the present invention that is pharmaceutically acceptable and has the desired pharmacological activity of the parent compound. In addition, pharmaceutically acceptable salts herein are intended to refer to all salts that can be used not only in pharmaceutical compositions, but also in cosmetic compositions or food compositions. The salt is not particularly limited as long as it is pharmaceutically acceptable, and for example, hydrochloric acid, sulfuric acid, nitric acid, phosphoric acid, hydrofluoric acid, hydrobromic acid, formic acid, acetic acid, tartaric acid, lactic acid, citric acid, fumaric acid, maleic acid, succinic acid, methanesulfonic acid, benzenesulfonic acid, toluenesulfonic acid, naphthalenesulfonic acid, and the like can be used.

The present invention provides a compound selected from the group consisting of compounds of the following formulas or a pharmaceutically acceptable salt thereof.

[Formula 3]

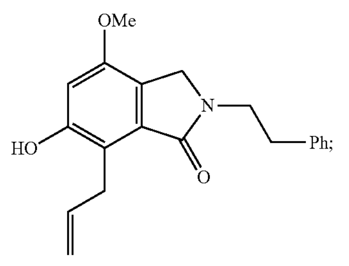

[Formula 6]

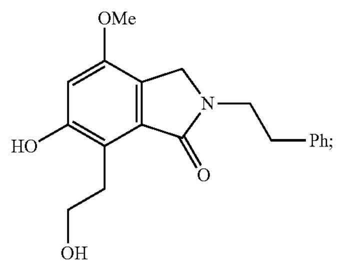

-continued
[Formula 7]
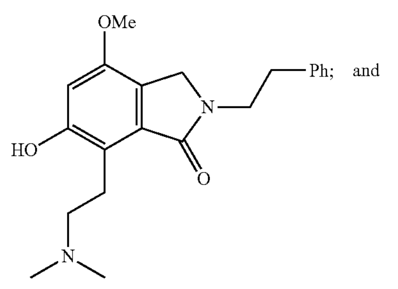
and
[Formula 8]
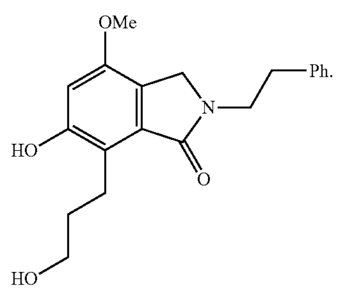
In one embodiment, the compounds of Formulas 3 and 6 above may be prepared according to Reaction Scheme 1 below.
[Reaction Scheme 1]
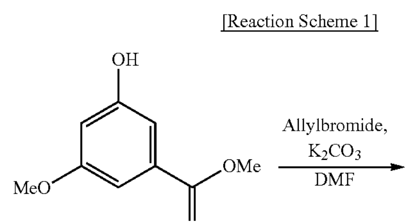
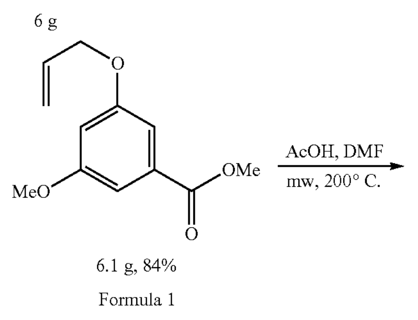
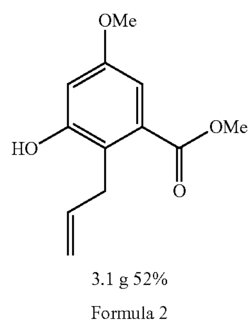
-continued
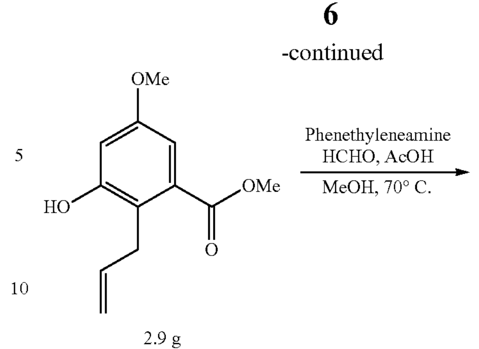
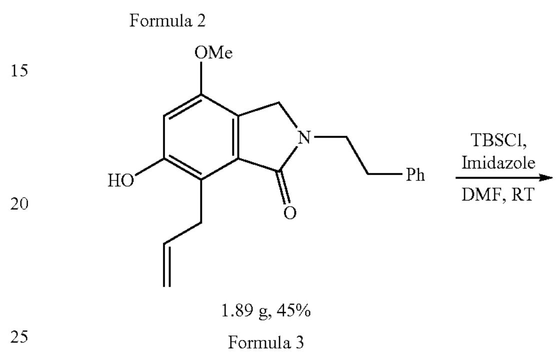
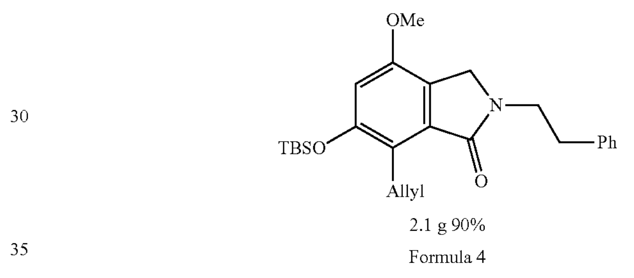
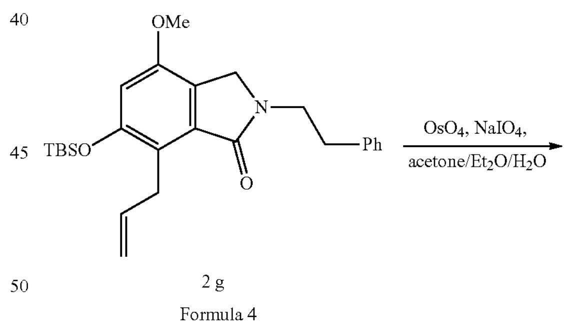
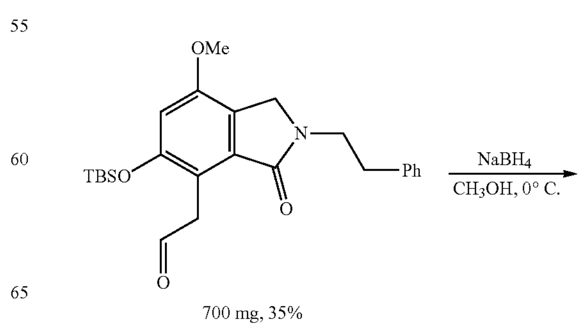

-continued

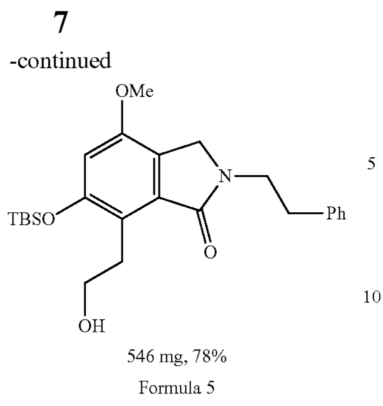

Formula 5

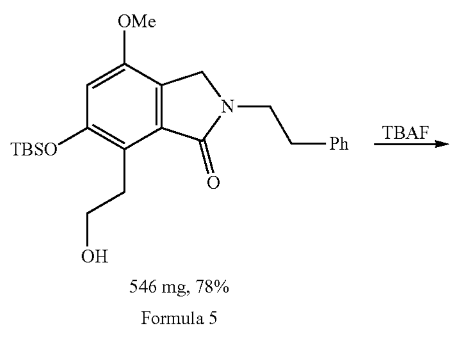

Formula 5

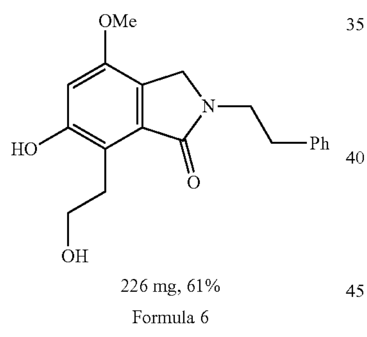

Formula 6

In one embodiment, the compound of Formula 7 above may be prepared according to Reaction Scheme 2 below.

[Reaction Scheme 2]

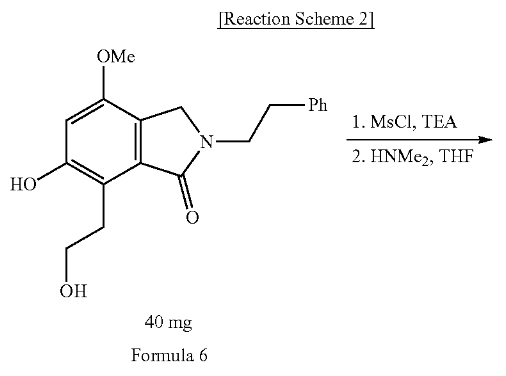

Formula 6

-continued

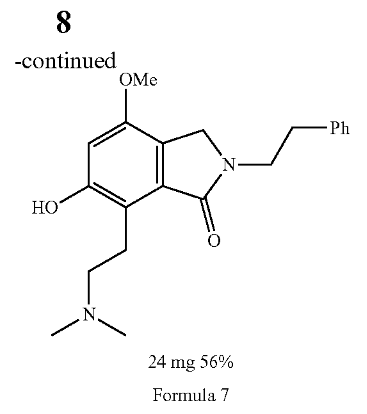

Formula 7

In one embodiment, the compound of Formula 8 above may be prepared according to Reaction Scheme 3 below.

[Reaction Scheme 3]

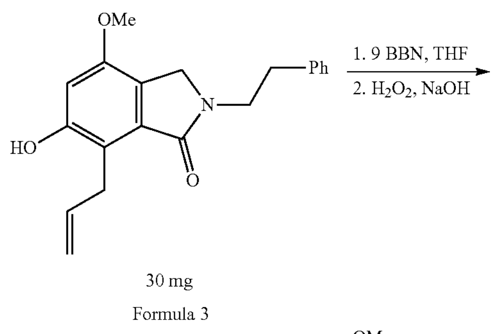

Formula 3

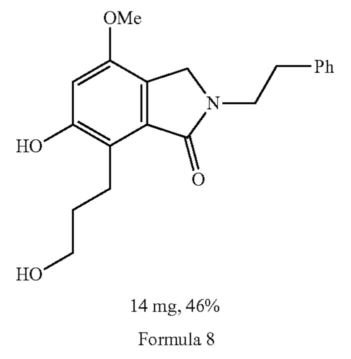

Formula 8

The present invention provides a pharmaceutical composition for preventing or treating neurological diseases, comprising the compound represented by Formula 9 or pharmaceutically acceptable salt thereof. In addition, the present invention provides a method for preventing or treating neurological diseases, comprising administering the pharmaceutical composition to a subject. The subject may be a mammal, including a human, who has been diagnosed with a neurological disease or is likely to develop a neurological disease.

In one embodiment, the compound represented by Formula 9 may promote the increase of nerve growth factor or promote the growth of nerve cells. In another embodiment, the compound represented by Formula 9 may have antineuritic activity.

The pharmaceutical composition of the present invention may comprise a pharmaceutically acceptable additive. The additive includes a stabilizer, a surfactant, a lubricant, a solubilizer, a buffering agent, a sweetener, a base, an adsorbent, a corrigent, a binder, a suspending agent, a curing agent, an antioxidant, a brightener, a fragrance, a flavoring agent, a pigment, a coating agent, a wetting agent, a moisture adjusting agent, a filler, an antifoaming agent, a cooling agent, a chewing agent, an antistatic agent, a coloring agent, a dragee, a tonicity agent, a softener, an emulsifier, an adhesive, a thickener, a foaming agent, a pH adjusting agent, an excipient, a dispersing agent, a disintegrant, a waterproofing agent, an antiseptic, a preservative, a solubilizing agent, a solvent, a flowing agent, and the like, but is not limited thereto.

The pharmaceutical composition of the present invention can be parenterally administered or orally administered depending on the desired method, and the dosage varies depending on the patient's weight, age, sex, health condition, diet, administration time, administration method, excretion rate, and severity of the disease. In addition, the therapeutically effective amount of the composition may vary depending on the administration method, the target site, and the condition of the patient, and when used in the human body, the dosage should be determined in an appropriate amount in consideration of safety and efficiency.

The present invention provides a food composition for preventing or improving neurological diseases, comprising the compound represented by Formula 9 or pharmaceutically acceptable salt thereof.

In one embodiment, the food composition may further comprise various nutrients, vitamins, minerals (electrolytes), flavors such as synthetic flavors and natural flavors, coloring agents and enhancers (cheese, chocolate, etc.), pectic acid and a salt thereof, alginic acid and a salt thereof, organic acids, protective colloidal thickeners, pH adjusting agents, stabilizers, antiseptics, glycerin, alcohol, carbonation agents used in carbonated beverages, and the like.

In one embodiment, the food composition includes a form such as a pill, a powder, a granule, a precipitate, a tablet, a capsule, a liquid, a paste, a gel, or a jelly, and the food to which the composition can be added includes, for example, various types of foods, such as beverages, chewing gum, tea, vitamin complexes, health supplementary food, and the like.

The formulation of the food composition is not particularly limited, but may be formulated into, for example, a tablet, a granule, a powder, a liquid such as a drink, a caramel, a gel, a bar, and the like. The food composition of each formulation may be formulated without difficulty by those of ordinary skill in the art depending on the formulation or purpose of use by selecting and blending ingredients commonly used in the field in addition to the active ingredient.

The present invention provides a feed composition for preventing or improving neurological diseases, comprising the compound represented by Formula 9 or pharmaceutically acceptable salt thereof.

The feed composition may be ingested by all non-human animals, such as non-human primates, sheep, dogs, cattle, horses, and the like.

As used herein, the term "prevention" refers to any action of inhibiting or delaying the onset of a disease by administration of a composition, and "treatment" refers to any action in which symptoms of a subject suspected of and suffering from a disease are improved or beneficially changed by administration of a composition, and "improvement" refers to any action that at least reduces a parameter related to a condition, for example, the severity of a symptom, by administration of a composition.

In one embodiment, the neurological disease may be a neurological disease associated with or accompanied by reduced nerve growth factor activity, decreased nerve growth factor, nerve cell death, neuritis or reduced function of nerve cells. Preferably, the neurological disease may be Alzheimer's disease, dementia, Parkinson's disease, epilepsy, neurological disorder, peripheral neuropathy, stroke or ischemic brain disease.

Definition

Unless defined otherwise, all technical terms used herein have the same meaning as commonly understood by those of ordinary skill in the art to which the present invention belongs. Moreover, numerical values described herein are considered to include the meaning of "about" unless explicitly stated otherwise. Definitions of moieties and substituents as used herein are provided below. Unless specified otherwise, each moiety has the following definitions and is used to have the same meaning as commonly understood by those of ordinary skill in the art.

As used herein, the term "Cx-y" or "Cx-Cy," when used in conjunction with a chemical moiety such as acyl, acyloxy, alkyl, haloalkyl, cycloalkyl, alkenyl, alkynyl or alkoxy, is intended to include a group containing from x to y carbons in the chain. $C_0$ alkyl represents hydrogen when the substituent is in the terminal position or a bond when the substituent is in the internal position. In addition, for example, a $C_1$-$C_6$ alkyl group contains from 1 to 6 carbon atoms in the chain.

As used herein, the term "alkyl" is a hydrocarbon having unsubstituted or substituted primary, secondary, tertiary and/or quaternary carbon atoms, and includes a saturated aliphatic group which may be straight-chain, branched or cyclic, or a combination thereof. For example, an alkyl group may have from 1 to 20 carbon atoms (i.e., $C_1$-$C_{20}$ alkyl), from 1 to 10 carbon atoms (i.e., $C_1$-$C_{10}$ alkyl), or from 1 to 6 carbon atoms (i.e., $C_1$-$C_6$ alkyl). Unless defined otherwise, in preferred embodiments, an alkyl refers to $C_1$-$C_6$ alkyl. Examples of suitable alkyl groups may include methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$), and octyl ($—(CH_2)_7CH_3$), and the like, but are not limited thereto.

Moreover, as used throughout the specification, examples and claims, the term "alkyl" is intended to include both unsubstituted and substituted alkyl groups, the latter of which refers to an alkyl moiety having a substituent that replaces a hydrogen on at least one carbon of the hydrocarbon backbone, which includes a haloalkyl group such as trifluoromethyl and 2,2,2-trifluoroethyl, and the like.

As used herein, the term "alkenyl" is a hydrocarbon that has primary, secondary, tertiary and/or quaternary carbon atoms, includes straight-chain, branched and cyclic groups, or a combination thereof, and has at least one unsaturated region, i.e., a carbon-carbon $sp^2$ double bond. For example, an alkenyl group may have from 2 to 20 carbon atoms (i.e., $C_2$-$C_{20}$ alkenyl), from 2 to 12 carbon atoms (i.e., $C_2$-$C_{12}$ alkenyl), from 2 to 10 carbon atoms (i.e., $C_2$-$C_{10}$ alkenyl), or from 2 to 6 carbon atoms (i.e., $C_2$-$C_6$ alkenyl). Examples of suitable alkenyl groups may include vinyl ($—CH{=}CH_2$), allyl ($—CH_2CH{=}CH_2$), cyclopentenyl ($—C_5H_7$), and 5-hexenyl ($—CH_2CH_2CH_2CH_2CH{=}CH_2$), but are not limited thereto.

As used herein, the term "alkynyl" is a hydrocarbon that has primary, secondary, tertiary and/or quaternary carbon atoms, includes straight-chain, branched and cyclic groups, or a combination thereof, and has at least one carbon-carbon sp triple bond. For example, an alkynyl group may have from 2 to 20 carbon atoms (i.e., $C_2$-$C_{20}$ alkynyl), from 2 to 12 carbon atoms (i.e., $C_2$-$C_{12}$ alkynyl), from 2 to 10 carbon atoms (i.e., $C_2$-$C_{10}$ alkynyl), or from 2 to 6 carbon atoms (i.e., $C_2$-$C_6$ alkynyl). Examples of suitable alkynyl groups may include acetylenic ($—C{\equiv}CH$) and propargyl ($—CH_2C{\equiv}CH$), but are not limited thereto.

As used herein, the term "alkoxy" refers to a group in which an alkyl group is attached to the parent compound through an oxygen atom, which may be represented by —O-alkyl, wherein the alkyl group is as defined herein and may be unsubstituted or substituted. The alkyl group of an alkoxy group may have, for example, from 1 to 20 carbon atoms (i.e., $C_1$-$C_{20}$ alkoxy), from 1 to 12 carbon atoms (i.e., $C_1$-$C_{12}$ alkoxy), from 1 to 10 carbon atoms (i.e., $C_1$-$C_{10}$ alkoxy), or from 1 to 6 carbon atoms (i.e., $C_1$-$C_6$ alkoxy). Examples of suitable alkoxy groups may include methoxy ($—O—CH_3$ or —OMe), ethoxy ($—OCH_2CH_3$ or -OEt), and t-butoxy ($—OC(CH_3)_3$ or —O-tBu), and the like, but are not limited thereto.

As used herein, the term "hydroxyalkyl" refers to an alkyl group substituted with a hydroxyl group, and may be represented by -alkyl-OH.

As used herein, the term "alkoxyalkyl" refers to an alkyl group substituted with an alkoxy group, as defined herein, and may be represented by -alkyl-O-alkyl.

Hereinafter, the present invention will be described in more detail through the examples, but the following examples are for illustrative purposes only and are not intended to limit the scope of the present invention.

[Example 1] Preparation of Compound of Formula 1

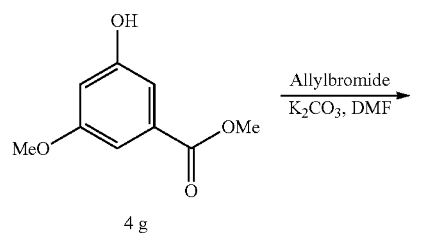

-continued

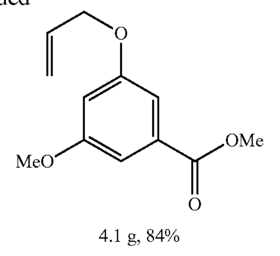

To a solution of methyl 3-hydroxy-5-methoxybenzoate (4 g, 21.96 mmol) in DMF was added 2.5 equivalents of potassium carbonate, and allyl bromide (6.64 g, 54.89 mmol) was added dropwise at room temperature. The reaction mixture was stirred for 15 hours at room temperature. The reaction was quenched by the addition of a saturated aqueous $NaHCO_3$ solution (30 mL) and washed with $CHCl_3$ (3×30 mL), and then the combined organic layers were dried over $MgSO_4$, filtered and concentrated. The crude product was purified by silica gel column chromatography (hexane/$Et_2O$, 20:1) to obtain methyl 3-(allyloxy)-5-methoxybenzoate (4.1 g, 84%) represented by Formula 1 as a white solid.

$^1$H NMR (400 MHz, $CDCl_3$); δ 7.17 (s, 1H), 6.65 (s, 1H), 6.01 (dd, J=11.4, 5.4 Hz, 1H), 5.34 (dd, J=49.4, 13.4 Hz, 2H), 4.53 (d, J=5.1 Hz, 2H), 3.84 (d, J=32.6 Hz, 3H), 3.80 (s, 3H). 13C NMR (100 MHz, $CDCl_3$); δ 168.85, 160.68, 159.65, 132.90, 132.04, 117.98, 107.97, 107.37, 106.50, 69.10, 55.62, 52.30.

[Example 2] Preparation of Compound of Formula 2

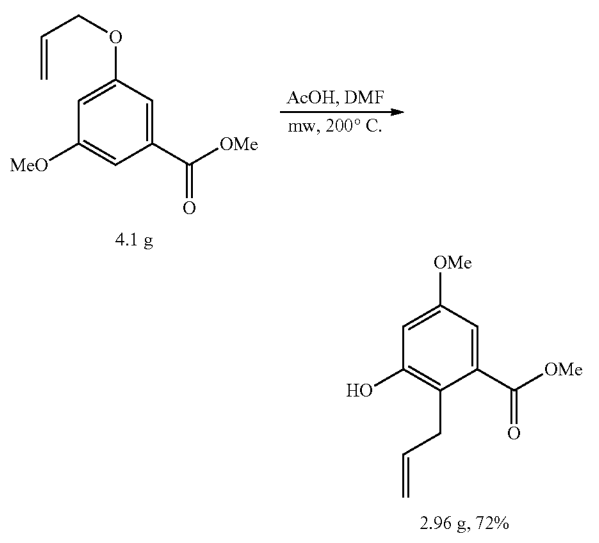

Methyl 3-(allyloxy)-5-methoxybenzoate (4.1 g, 18.45 mmol) represented by Formula 1 was refluxed in DMF (10 mL) and AcOH (2 ml) for 1 day. The cooled reaction mixture was concentrated in vacuo and dissolved in AcOEt (30 ml). The organic layer was washed with a saturated aqueous NaCl solution (100 ml), and then dried over $MgSO_4$, and concentrated. The crude product was purified by silica gel column chromatography using a 1:3 mixture of AcOEt and hexane as an eluent to obtain methyl 2-allyl-3-hydroxy-5-methoxybenzoate (2.96 g, 72%) represented by Formula 2 as a white solid.

$^1$H NMR (400 MHz, $CDCl_3$); δ 7.19 (d, J=1.4 Hz, 1H), 7.16 (d, J=1.4 Hz, 1H), 5.94 (dd, J=16.8, 10.4 Hz, 1H), 5.14-5.02 (m, 2H), 3.92-3.86 (m, 3H), 3.86 (d, J=6.5 Hz, 3H), 3.47 (dt, J=6.1, 1.6 Hz, 2H). 13C NMR (100 MHz, $CDCl_3$); δ 167.05, 158.22, 154.93, 135.46, 129.43, 119.36, 115.84, 110.27, 104.34, 56.06, 52.28, 27.66.

[Example 3] Preparation of Compound of Formula 3

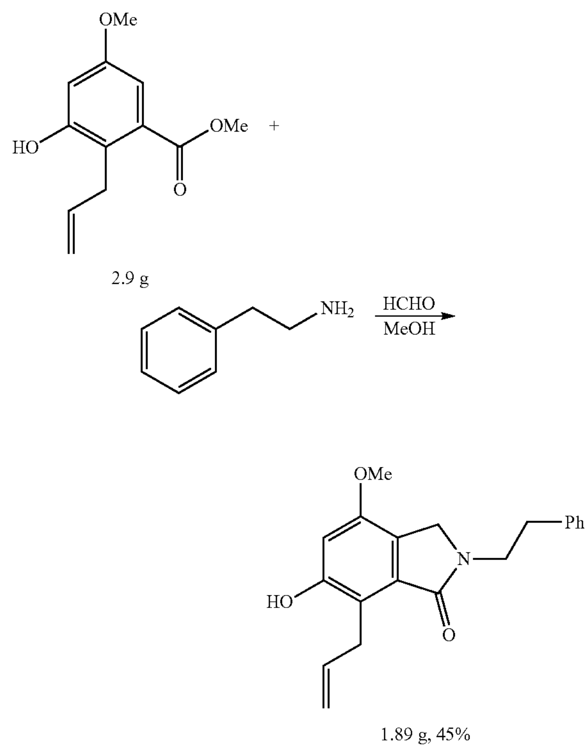

To a solution of methyl 2-allyl-3-hydroxy-5-methoxybenzoate (2.9 g, 13.05 mmol) represented by Formula 2 in methanol (10 ml) was added 2 equivalents (3.16 g, 26.12 mmol) of phenylethanamine, and a 30% formaldehyde solution (4.0 mL) was added dropwise at room temperature. The reaction mixture was warmed to 60° C. and stirred for 12 hours. After confirming the reaction completion by TLC, the reaction mixture was cooled back to room temperature and quenched by the slow addition of a saturated aqueous solution of sodium hydrogen carbonate. The aqueous layer was extracted three times with EtOAc, and the combined organic layers were washed with brine, dried over sodium sulfate, evaporated, and then purified by column chromatography to obtain 7-allyl-6-hydroxy-4-methoxy-2-phenethyl isoindolin-1-one (1.89 g, 45%) represented by Formula 3 as a white solid.

$^1$H NMR (400 MHz, DMSO-$d_6$); δ 9.54 (s, 1H), 7.32-7.17 (m, 5H), 6.57 (s, 1H), 5.83 (dd, J=17.1, 10.1 Hz, 1H), 4.96-4.70 (m, 2H), 4.07 (s, 2H), 3.72 (s, 3H), 3.69-3.62 (m, 4H), 2.85 (t, J=7.4 Hz, 2H). 13C NMR (100 MHz, $CDCl_3$); δ 168.96, 157.86, 156.62, 153.60, 138.86, 136.91, 128.78, 128.69, 126.55, 122.25, 116.35, 114.64, 102.11, 55.55, 47.10, 44.31, 34.92, 27.49.

[Example 4] Preparation of Compound of Formula 4

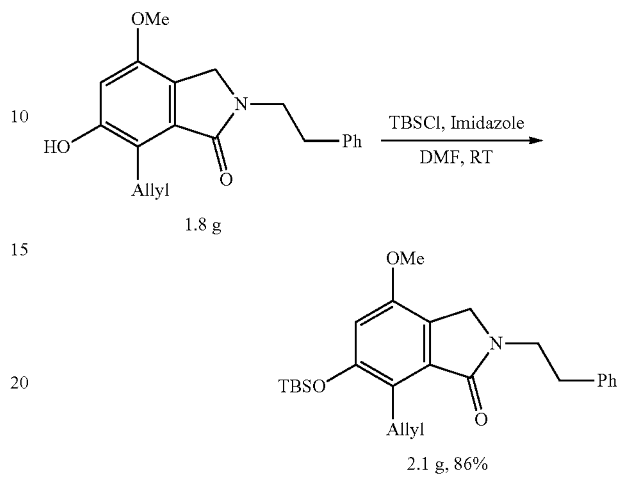

To a solution of 7-allyl-6-hydroxy-4-methoxy-2-phenethyl isoindolin-1-one (1.8 g, 5.57 mmol) represented by Formula 3 and 1H imidazole (2.5 equivalents) in $CH_2Cl_2$ (25 mL) was added tert-butyldimethylchlorosilane (1.67 g, 11.14 mmol). The reaction mixture was stirred for 2 hours at room temperature. The reaction was quenched by the addition of a saturated aqueous $NaHCO_3$ solution (30 mL) and washed with $CH_2Cl_2$ (3×30 mL). The combined organic layers were dried over $MgSO_4$, filtered and concentrated. The crude product was purified by silica gel column chromatography (hexane/$Et_2O$, 20:1) to obtain 7-allyl-6-((tert-butyldimethylsilyl)oxy)-4-methoxy-2-phenethyl isoindolin-1-one (2.1 g, 86%) represented by Formula 4 as a white solid.

$^1$H NMR (400 MHz, $CDCl_3$); δ 7.33-7.15 (m, 5H), 6.47 (s, 1H), 6.00 (ddt, J=16.3, 10.1, 6.2 Hz, 1H), 5.09-4.83 (m, 2H), 4.09 (s, 2H), 3.86 (d, J=6.1 Hz, 2H), 3.82-3.71 (m, 5H), 2.99-2.91 (m, 2H), 1.07-0.99 (m, 9H), 0.23 (s, 6H). 13C NMR (100 MHz, $CDCl_3$); δ 168.82, 154.78, 152.62, 138.96, 137.49, 131.73, 128.74, 126.50, 122.49, 121.52, 114.48, 104.77, 55.38, 47.15, 44.26, 34.91, 27.69, 25.90, 18.39, 1.11, −3.93.

[Example 5] Preparation of Compound of Formula 5

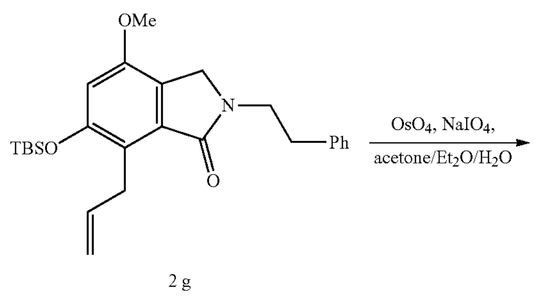

-continued

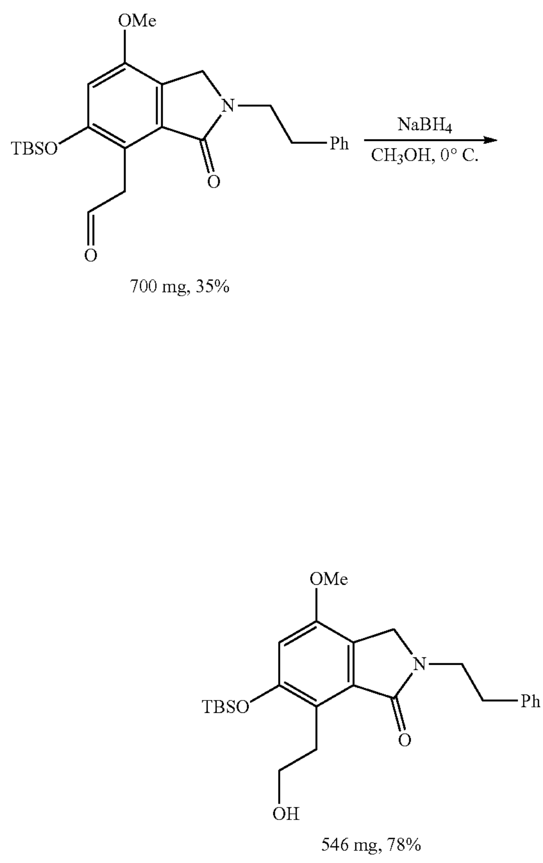

7-allyl-6-((tert-butyldimethylsilyl)oxy)-4-methoxy-2-phenethyl isoindolin-1-one (2 g, 4.55 mmol) represented by Formula 4 was added to $Et_2O$ (24 mL), and then to the solution was added a 0.05M solution of 0504 (2.5 equivalents) in acetone. The resulting dark brown solution was stirred for 10 minutes, and water (24 mL) was added, and then finely powdered $NaIO_4$ (4.85 g, 22.77 mmol) was added in 5 portions over 5 hours. The tan slurry was stirred for additional 3 hours, and then diluted with $Et_2O$, and the layers were separated. The organic layer was washed with saturated brine, dried over $Na_2SO_4$, filtered, and then concentrated in vacuo. The crude product was dissolved in $CH_3OH$ (6.0 mL), cooled to 0° C., and then treated with $NaBH_4$ (121 mg, 3.18 mmol). After 30 minutes, the excess hydride was quenched by the addition of 10% HCl, and the resulting mixture was extracted with $Et_2O$. The combined organic extracts were washed with saturated brine, dried over $Na_2SO_4$, filtered through a $SiO_2$ plug (1.0 in.) over a pad of Celite, and then concentrated in vacuo to obtain 6-((tert-butyldimethylsilypoxy)-7-(2-hydroxyethyl)-4-methoxy-2-phenethyl isoindolin-1-one (546 mg, 78%) represented by Formula 5 as a white solid.

$^1$H NMR (400 MHz, DMSO-$d_6$); δ 9.56 (s, 1H), 7.33-7.12 (m, 5H), 6.56 (d, J=3.9 Hz, 1H), 4.05 (s, 2H), 3.72-3.62 (m, 5H), 3.57-3.51 (m, 2H), 3.14 (d, J=7.1 Hz, 2H), 2.85 (t, J=7.3 Hz, 2H), 0.80 (d, J=3.3 Hz, 9H), −0.03 (s, 6H). 13C NMR (100 MHz, $CD_3OD$); δ 169.31, 159.85, 149.20, 139.05, 131.84, 124.60, 122.10, 98.32, 96.20, 60.18, 55.10, 50.01, 48.30, 48.09, 44.02, 34.39, 27.58, 25.12, 18.18, −4.52.

[Example 6] Preparation of Compound of Formula 6

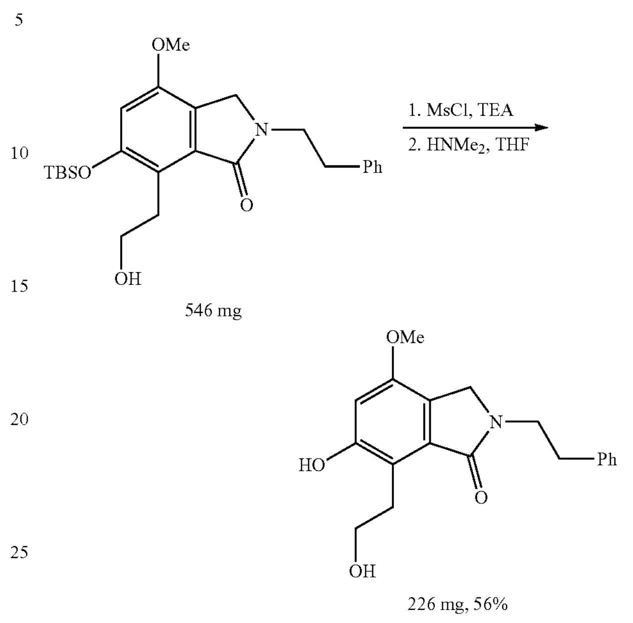

To a solution of 6-((tert-butyldimethylsilypoxy)-7-(2-hydroxyethyl)-4-methoxy-2-phenethyl isoindolin-1-one (546 mg, 1.23 mmol) represented by Formula 5 in THF at 0° C. was added dropwise 1.85 mL (1.85 mmol) of a 1.0 M solution of tetra-n-butylammonium fluoride in THF. The solution was warmed to room temperature for 1 hour and added to a saturated solution of $NH_4Cl$. The mixture was extracted with $Et_2O$, and then the combined organic layers were dried over $Na_2SO_4$, filtered, and then concentrated in vacuo to give an oil, which was purified by $SiO_2$ chromatography (50% EtOAc/hexane) to obtain 6-hydroxy-7-(2-hydroxyethyl)-4-methoxy-2-phenethyl isoindolin-1-one (226 mg, 56%) represented by Formula 6.

$^1$H NMR (400 MHz, DMSO-$d_6$); δ 9.56 (s, 1H), 7.29-7.13 (m, 5H), 6.57 (s, 1H), 4.67 (s, 1H), 4.06 (s, 2H), 3.71 (s, 3H), 3.65 (t, J=7.4 Hz, 2H), 3.39 (d, J=7.7 Hz, 2H), 3.13 (t, J=7.5 Hz, 2H), 2.85 (t, J=7.4 Hz, 2H). $^{13}$C NMR (100 MHz, DMSO-$d_6$); δ 168.50, 157.33, 152.98, 139.64, 131.75, 129.12, 128.93, 126.75, 120.43, 115.51, 102.02, 61.82, 55.70, 46.74, 43.68, 34.37, 27.00.

[Example 7] Preparation of Compound of Formula 7

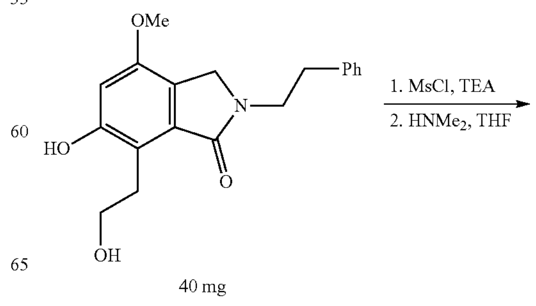

-continued

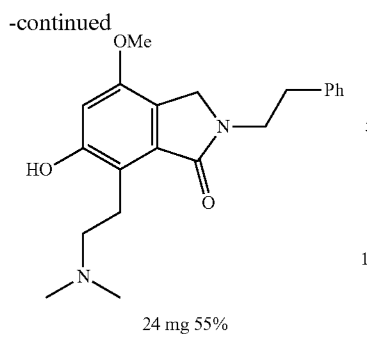

6-hydroxy-7-(2-hydroxyethyl)-4-methoxy-2-phenethyl isoindolin-1-one (40 mg, 0.12 mmol) represented by Formula 6 was added to THF at room temperature, and then MsCl followed by TEA were added dropwise to the reaction mixture, and then stirred for 3 hours. Upon formation of the starting material, the reaction mixture was cooled to 0° C., and dimethylamine in THF was added to the reaction, and then the reaction mixture was stirred for 6 hours at 60° C. The reaction was quenched with brine (30 mL) and washed with $CHCl_3$ (3×30 mL). The combined organic layers were dried over $MgSO_4$, filtered and concentrated. The crude product was purified by column chromatography to obtain 7-(2-(dimethylamino)ethyl)-6-hydroxy-4-methoxy-2-phenethyl isoindolin-1-one (24 mg, 55%) represented by Formula 7 as a white solid.

$^1$H NMR (400 MHz, $CDCl_3$); δ 7.33-7.16 (m, 5H), 7.04 (s, 1H), 4.46 (t, J=7.1 Hz, 2H), 4.14 (s, 2H), 3.86 (s, 3H), 3.81 (t, J=7.4 Hz, 2H), 3.57 (t, J=7.1 Hz, 2H), 3.34 (s, 3H), 3.01-2.93 (m, 5H). 13C NMR (100 MHz, $CDCl_3$); δ 167.58, 153.75, 148.15, 138.49, 132.59, 129.09, 128.76, 126.74, 119.62, 107.60, 69.84, 55.98, 47.56, 44.28, 38.75, 37.40, 34.81, 29.78, 24.48.

[Example 8] Preparation of Compound of Formula 8

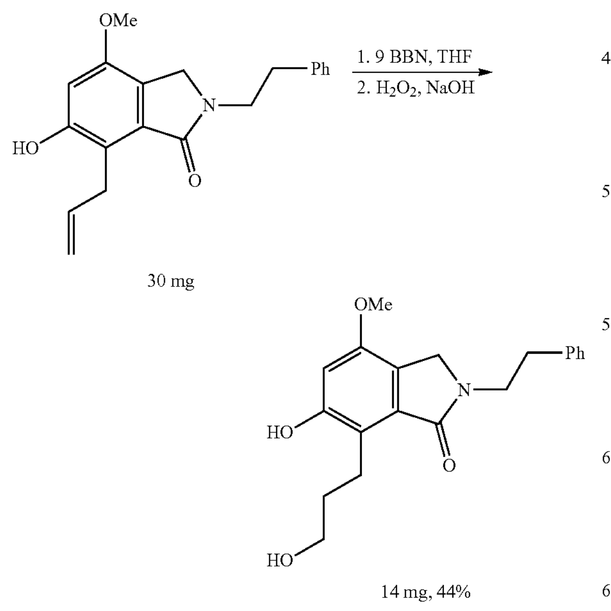

To a solution of 7-allyl-6-hydroxy-4-methoxy-2-phenethyl isoindolin-1-one (30 mg, 0.09 mmol) represented by Formula 3 in THF at 0° C. was added dropwise 9 BBN (2.5 equivalents) in THF. The reaction mixture was stirred at room temperature for 5 hours. The reaction was quenched by the addition of a saturated aqueous solution of $H_2O_2$ (5 equivalents) and NaOH (3 mL, 2 M) and stirred for 3 hours. The reaction mixture was washed with $CHCl_3$ (3×30 mL). The combined organic layers were dried over $MgSO_4$, filtered and concentrated. The crude product was purified by silica gel column chromatography (hexane/$Et_2O$, 5:1) to obtain 6-hydroxy-7-(3-hydroxypropyl)-4-methoxy-2-phenethyl isoindolin-1-one (14 mg, 44%) represented by Formula 8 as a white solid.

$^1$H NMR (400 MHz, $CDCl_3$) δ 7.34-7.09 (m, 1H), 6.58 (s, 1H), 4.10 (s, 1H), 3.89-3.70 (m, 1H), 3.55 (t, J=5.4 Hz, 1H), 3.35-3.21 (m, 1H), 3.10-2.93 (m, 1H), 1.93 (td, J=11.1, 6.1 Hz, 1H). 13C NMR (100 MHz, $CDCl_3$) δ 169.45, 156.59, 153.23, 138.77, 131.79, 128.73, 126.56, 122.03, 116.95.

[Experimental Example 1] Evaluation of Ability to Promote Increase of Nerve Growth Factor and Cytotoxicity In order to measure the amount of nerve growth factor (NGF) produced in the cell medium and to confirm the effect on cell viability when cells were treated with the compounds of the present invention, the following experiments were performed.

Evaluation of Ability to Promote Increase of Nerve Growth Factor (NGF)

Rat astrocyte-derived C6 glioma cells were dispensed in DMEM culture solution at a concentration of $1\times10^5$ cells/well in a 24 well plate and stabilized overnight, and then treated with the compounds of Formulas 3, 6, 7, and 8 at a concentration of 10 μM, and reacted in a 37° C. incubator for 24 hours. The treated medium was collected and centrifuged, and then absorbance was measured using an enzyme linked immunoassay kit (ELISA kit).

Figure 9:
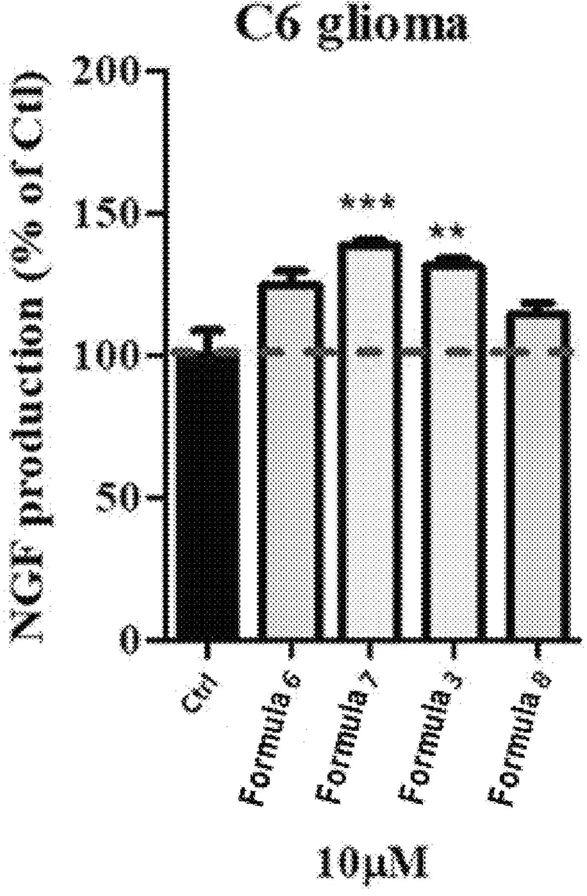
FIG. 9 is a graph showing the amount of nerve growth factor produced in C6 glioma cells.

As shown in FIG. 9, it was found that the nerve growth factor produced in the cell medium was increased when treated with the compounds of the present invention, and in particular, it was found that the increased production of nerve growth factor was significantly excellent when treated with the compounds of Formulas 3 and 7.

Evaluation of Cytotoxicity

Rat astrocyte-derived C6 glioma cells were dispensed in DMEM culture solution at a concentration of $1\times10^5$ cells/well in a 96 well plate and stabilized overnight, and then treated with the compounds of Formulas 3, 6, 7, and 8 at a concentration of 10 μM, and reacted for 24 hours. The culture solution was removed, and then 100 μl of MTT solution at a concentration of 0.5 mg/ml was added to each well and incubated for at least 1 hour in a 37° C. incubator, and then MTT was removed, and DMSO was dispensed in 200 μl, and absorbance of formazin produced in the well was measured at 540 nm using an ELISA reader.

Figure 10:
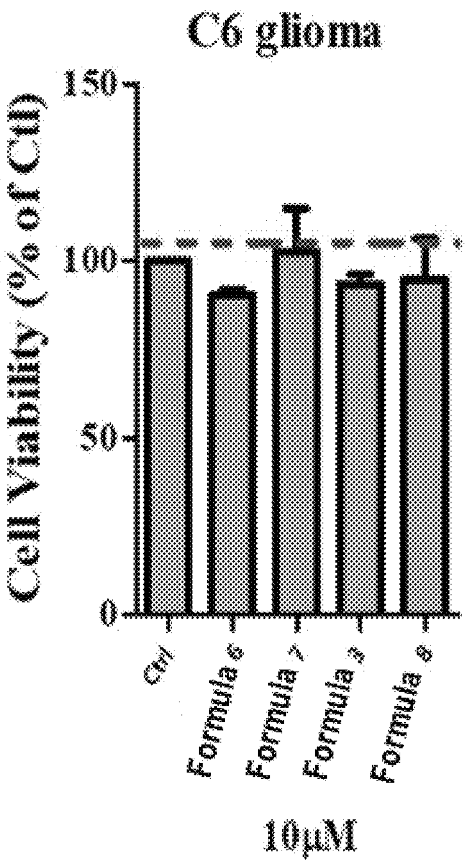
FIG. 10 is a graph showing the results of cytotoxicity evaluation in C6 glioma cells.

As shown in FIG. 10, when treated with all the compounds, there was no significant difference in cell viability from that of the control group, and thus, it was found that the compounds of the present invention did not exhibit cytotoxicity.

[Experimental Example 2] Evaluation of Ability to Promote Growth of Nerve Cells and Cytotoxicity In order to measure the growth degree of neurite and to confirm the effect on cell viability when N2a cells were treated with the compounds of the present invention, the following experiments were performed. Cerebrolysin, which has an effect of improving neurological dysfunction and is used as a therapeutic agent for diseases related to brain dysfunction, was used as a positive control group.

Analysis of Neurite Growth

N2a cells (Neuro-2a cells) were coated with a solution of Poly-D-lysin (100 μg/ml) in a 24 well plate overnight, washed with sterile water, and then incubated for 1 hour. Nerve cells were dispensed in DMEM at a concentration of $15\times10^3$ cells/well or $30\times10^3$ cells/well and stabilized overnight, and then treated with the compounds of Formulas 3, 6, 7, and 8 at a concentration of 10 μM, and the growth of neurites was measured every 2 hours using the Incucyte zoom live cell analysis system.

Figure 11A:
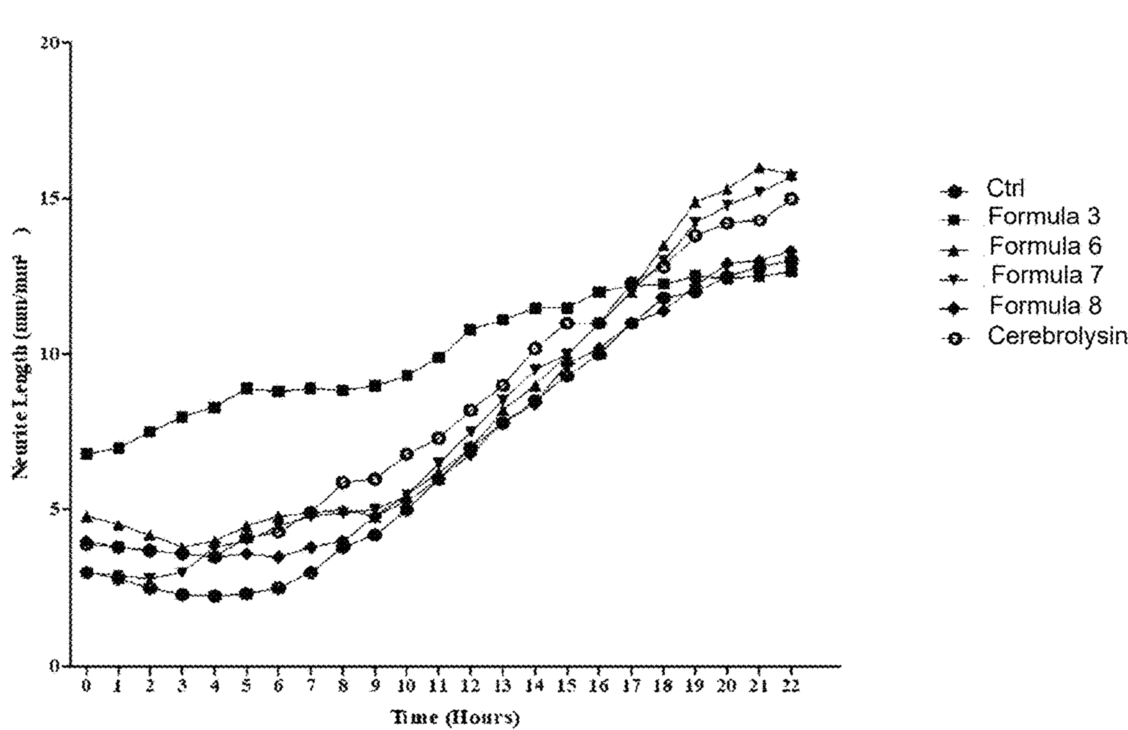
FIGS. 11*a* to 11*c* show the results obtained by measuring neurite growth in N2a cells.
Figure 11B:
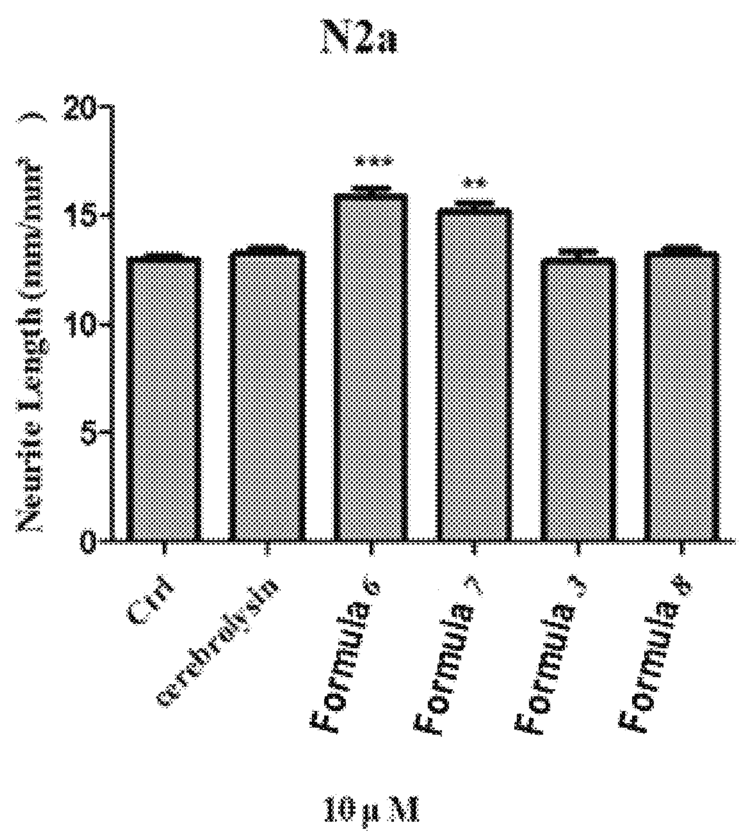
Figure 11C:
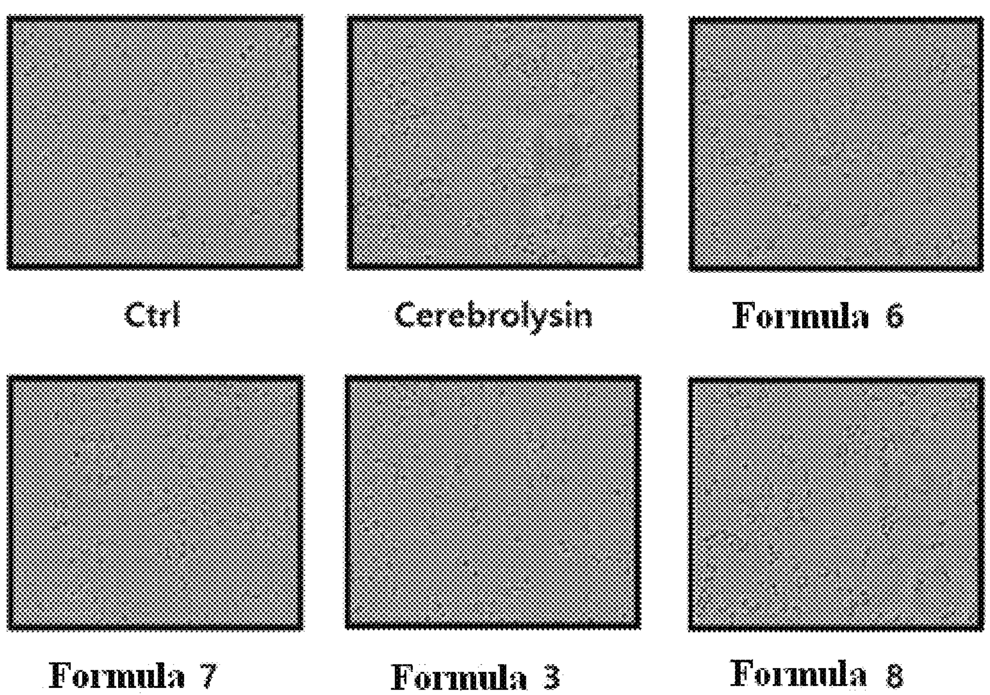

As shown in FIGS. 11*a* to 11*c*, it was found that the growth of neurites was increased when treated with the compounds of the present invention. Therefore, it was found that the compounds of the present invention are effective for neurotrophic factors and promote the growth of nerve cells.

Evaluation of Cytotoxicity

N2a cells were dispensed in DMEM culture solution at a concentration of $1\times10^5$ cells/well in a 96 well plate and stabilized overnight, and then treated with the compounds of Formulas 3, 6, 7, and 8 at a concentration of 10 μM, and reacted for 24 hours. The culture solution was removed, and then 100 μl of MTT solution at a concentration of 0.5 mg/ml was added to each well and incubated for at least 1 hour in a 37° C. incubator, and then MTT was removed, and DMSO was dispensed in 200 μl, and absorbance of formazin produced in each well was measured at 540 nm using an ELISA reader.

Figure 12:
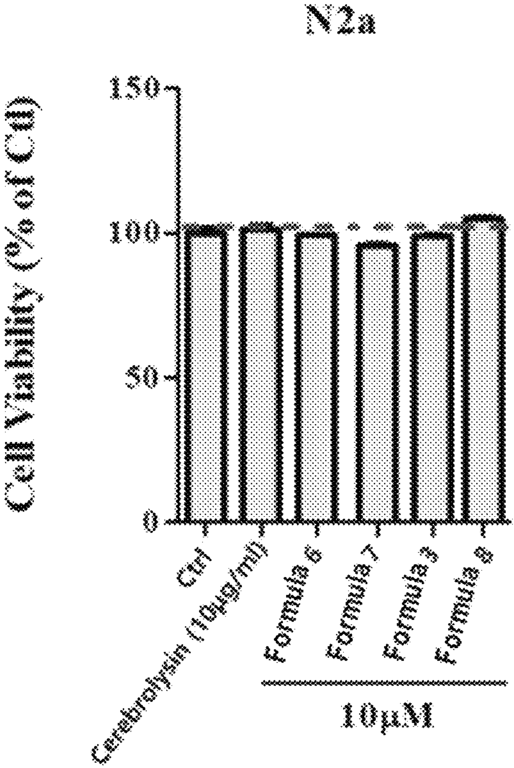
FIG. 12 is a graph showing the results of cytotoxicity evaluation in N2a cells.

As shown in FIG. 12, when treated with all the compounds, there was no significant difference in cell viability from that of the control group, and thus, it was found that the compounds of the present invention did not exhibit cytotoxicity to nerve cells.

[Experimental Example 3] Analysis of NO Production and Evaluation of Cytotoxicity In order to confirm the change in NO production and the effect on cell viability when BV2 cells were treated with the compounds of the present invention, the following experiments were performed. L-NMMA (NG-monomethyl-L-arginine), an NO synthesis inhibitor, was used as a positive control group.

Analysis of NO production for evaluation of antineuritic activity BV2 cells (microglia) were dispensed in DMEM culture solution at a concentration of $6\times10^4$ cells/well in a 96 well plate, and then treated with the compounds of Formulas 6, 7, and 8 at a concentration of 10 NM, and incubated for 24 hours. After 24 hours, each sample was treated with a concentration of 10 NM, reacted for 1 hour, and then stimulated with 100 ng/ml of LPS for 24 hours. The production of nitrite, a soluble oxidation product of NO (nitric oxide), was measured in the culture medium through the Griess reaction.

Figure 13:
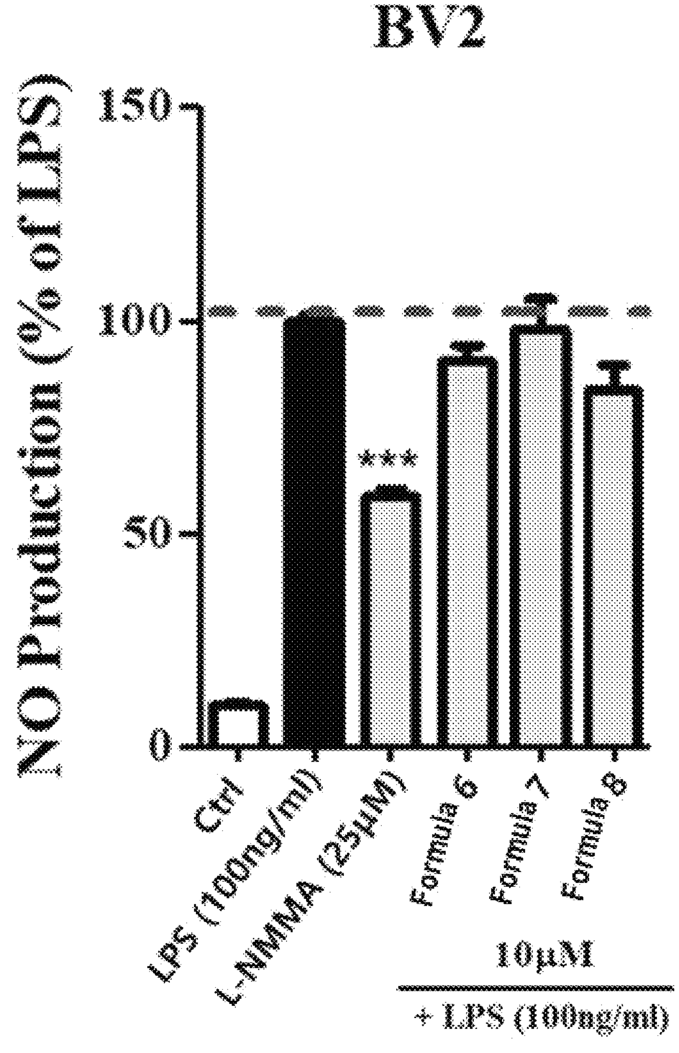
FIG. 13 is a graph showing the amount of NO production measured in BV2 cells.

As shown in FIG. 13, it was found that when treated with the compounds of Formulas 6, 7, and 8, NO production was reduced compared to that of the untreated control group. Therefore, it was found that the compounds of the present invention have an antineuritic effect.

Evaluation of Cytotoxicity

BV2 cells were dispensed in DMEM culture solution at a concentration of $1\times10^5$ cells/well in a 96 well plate and stabilized overnight, and then treated with the compounds of Formulas 3, 6, 7, and 8 at a concentration of 10 μM, and then reacted for 24 hours. The culture solution was removed, and then 100 μl of MTT solution at a concentration of 0.5 mg/ml was added to each well and incubated for at least 1 hour in a 37° C. incubator, and then MTT was removed, and DMSO was dispensed in 200 μl, and absorbance of formazin produced in each well was measured at 540 nm using an ELISA reader.

Figure 14:
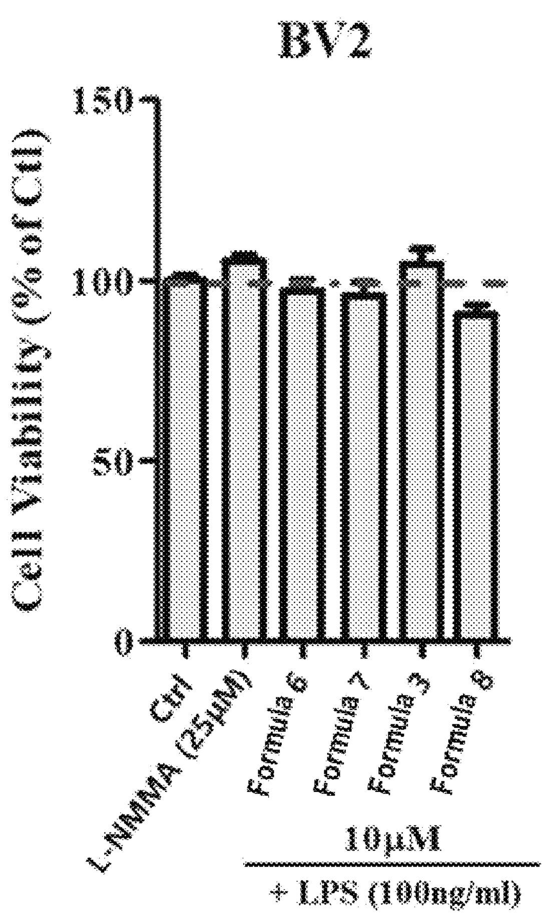
FIG. 14 is a graph showing the results of cytotoxicity evaluation in BV2 cells.

As shown in FIG. 14, when treated with all the compounds, there was no significant difference in cell viability from that of the control group, and thus, it was found that the compounds of the present invention did not exhibit cytotoxicity to microglia.

The invention claimed is:

1. A compound represented by Formula 9 below or a pharmaceutically acceptable salt thereof:

[Formula 9]

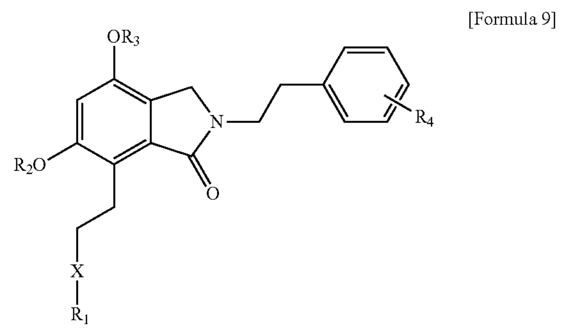

in the formula, $R_1$ is hydrogen, alkyl, alkenyl, alkynyl, hydroxy, alkoxy, hydroxyalkyl, alkoxyalkyl, or —N(Ra)(Rb);

$R_2$, $R_3$, $R_4$, Ra and Rb are each independently hydrogen or alkyl; and

X is a single bond or a double bond.

2. The compound or pharmaceutically acceptable salt thereof according to claim 1, wherein $R_1$ is hydrogen, alkyl, alkenyl, alkynyl, hydroxy, alkoxy, hydroxyalkyl, alkoxyalkyl, or —N(Ra)(Rb);

Ra and Rb are each independently hydrogen or alkyl;

$R_2$ and $R_4$ are hydrogen;

$R_3$ is alkyl; and

X is a single bond or a double bond.

3. The compound or pharmaceutically acceptable salt thereof according to claim 1, wherein $R_1$ is $C_1$-$C_6$ alkyl, hydroxy, $C_1$-$C_6$ hydroxyalkyl, or —N(Ra)(Rb);

Ra and Rb are each independently $C_1$-$C_6$ alkyl;

$R_2$ and $R_4$ are hydrogen;

$R_3$ is $C_1$-$C_6$ alkyl; and

X is a single bond or a double bond.

4. A compound selected from the group consisting of compounds of the following formulas or a pharmaceutically acceptable salt thereof:

[Formula 3]

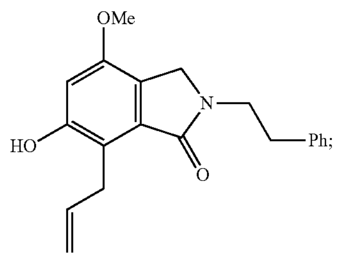

[Formula 6]

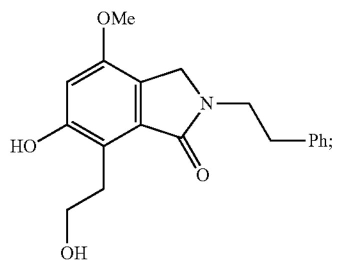

[Formula 7]

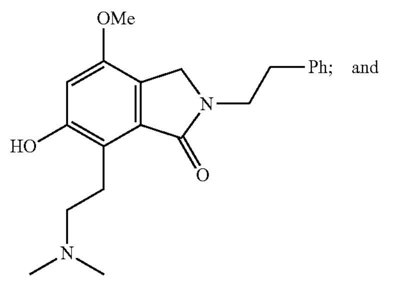

and

-continued

[Formula 8]

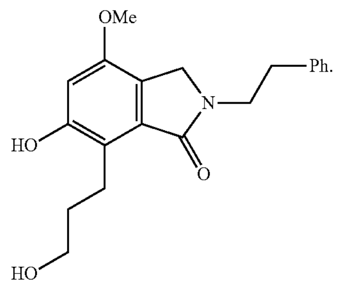

5. A pharmaceutical composition for preventing or treating neurological diseases, comprising the compound represented by Formula 9 or the pharmaceutically acceptable salt thereof according to claim 1.

6. A food composition for preventing or improving neurological diseases, comprising the compound represented by Formula 9 or the pharmaceutically acceptable salt thereof according to claim 1.

7. A feed composition for preventing or improving neurological diseases, comprising the compound represented by Formula 9 or the pharmaceutically acceptable salt thereof according to claim 1.

8. A method for preventing or treating neurological diseases, the method comprising administering the compound represented by Formula 9 or the pharmaceutically acceptable salt thereof according to claim 1 to a subject in need thereof.

9. A method for preventing or treating neurological diseases, the method comprising administering the compound or the pharmaceutically acceptable salt thereof according to claim 4 to a subject in need thereof.

* * * * *